(12) United States Patent
Meyer et al.

(10) Patent No.: US 6,683,231 B2
(45) Date of Patent: Jan. 27, 2004

(54) HIGH LEVEL PRODUCTION OF P-HYDROXYBENZOIC ACID IN GREEN PLANTS

(75) Inventors: Knut Meyer, Wilmington, DE (US); Paul V. Viitanen, West Chester, PA (US); Drew E. Van Dyk, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 45 days.

(21) Appl. No.: 09/855,341

(22) Filed: May 15, 2001

(65) Prior Publication Data

US 2002/0002715 A1 Jan. 3, 2002

Related U.S. Application Data

(60) Provisional application No. 60/209,854, filed on Jun. 2, 2000.

(51) Int. Cl.[7] .......................... A01H 1/00; C12P 21/06; C12N 15/82; C07H 21/04
(52) U.S. Cl. .................. 800/278; 800/287; 435/69.1; 435/69.7; 435/468; 536/23.6
(58) Field of Search .................. 800/288, 278, 800/298, 312, 322, 314, 320.1, 317.3, 320.2, 320.3, 313; 435/69.7, 69.8; 536/23.1

(56) References Cited

U.S. PATENT DOCUMENTS

| | | | |
|---|---|---|---|
| 5,717,084 A | 2/1998 | Herrera-Estrella et al. | 536/23.4 |
| 5,728,925 A | 3/1998 | Herrera-Estrella et al. | 800/205 |
| 6,030,819 A | 2/2000 | Amaratunga et al. | 435/132 |

FOREIGN PATENT DOCUMENTS

| | | |
|---|---|---|
| DE | 44 23 022 C 1 | 5/1995 |
| EP | 0189707 | 8/1993 |
| JP | 05328981 | 12/1993 |
| JP | 05336979 | 12/1993 |
| JP | 05336980 | 12/1993 |
| JP | 06078780 | 3/1994 |
| WO | WO 9600708 A | 1/1996 |
| WO | WO9856920 | 12/1998 |

OTHER PUBLICATIONS

Siebert et al., FEBS Lett 307:347–350 (1992).
Nichlols et al., J. Bacteriol 174:5309–5316 (1992).
Siebert et al., Microbiology 140: 897–904 (1992).
Walsh et al., Chem Rev. 90:1105–1129 (1990).
Schnitzler et al., Planta, 188:594–600 (1992).
Lydon et al., J. Agric. Food. Chem., 36:813–818.
Terashima et al., Phytochemistry, 14:1991–1992 (1975).
Loscher and Heide, Plant Physiol. 106:271–279 (1992).
Siebert et al., Plant Physiol. 112: 811–819 (1996).
Sommer et al., Plant Cell Physiol. 39(11): 1240–1244 (1998).
Kazufumi Yazaki, (Baiosaiensu to Indasutori (1998) 56(9), 621–622—Translated.
Li, et al., Plant Cell Physiol. 38(7):844–850 (1997).
Sommer et al., Plant Cell Reports 17:891–896(1998).
Sommer et al., Plant Molecular Biology 39:683–693 (1999).
Chua and Schmidt, Proc. Natl. Acad. Sci. 75: 6110–6114 (1978).
Highfield and Ellis, Nature 271:420–424 (1978.
Cline et al., J. Biol. Chem. 260:3691–3696 (1985).
Grossman et al., Nature 285: 625–628 (1980).
Van den Broeck et al., Nature 313: 358–362 (1985).
Schreier et al., EMBO J. 4:25–32 (1985).
Wasmann et al. Mol. Gen. Genet. 205–446–453 (1986).
Lubben et al., The Plant Cell 1: 1223–1230 (1989).
Robinson and Ellis, Eur. J. Biochem. 142:343–346 (1984).
Robinson and Ellis, Eur. J. Biochem. 152: 67–73 (1985).
Wasmann et al., J. Biol. Chem. 263:617–619 (1988).

*Primary Examiner*—Phuong T. Bui
*Assistant Examiner*—Stuart F Braum

(57) ABSTRACT

The invention relates to high-level production of pHBA in green plants using a unique expression cassette. The latter comprises a chorismate pyruvate lyase (CPL) coding sequence operably linked to a suitable promoter capable of driving protein expression in higher plants. Additionally, the CPL cassette comprises a sequence encoding a chloroplast transit peptide, its natural cleavage site, and a small portion of the transit peptide donor protein fused to the N-terminus of CPL. The chloroplast targeting sequence targets the foreign protein to the chloroplast compartment and aids in its uptake into the organelle. The cleavage site is unique to the transit peptide, and cleavage of the chimeric protein encoded by the cassette at this site releases a novel polypeptide that has full enzyme activity, comprising the mature CPL enzyme and a small portion of the transit peptide donor.

7 Claims, 7 Drawing Sheets

```
MASSVISSAA VATRSNVTQA SMVAPFTGLK SSATFPVTKK QNLDITSIAS           50
MASSVISSAA VATRSNVTQA SMVAPFTGLK SSATFPVTKK QNLDITSIAS           50
MASSVISSAA VATRSNVTQA SMVAPFTGLK SSATFPVTKK QNLDITSIAS           50
            ⇩
NGGRVSCM.. ..QVWPPINM KKYETLSYLP DLSDEQLLSE IEYLLKNGWV           96
NGGRVSCM.. ..QVWHMSHP ALTQLRALRY CKEIPALDPQ LLDWLLLEDS           96
NGGRVSCAVP CNGEFGMSHP ALTQLRALRY CKEIPALDPQ LLDWLLLEDS          100
.......... .....MSHP  ALTQLRALRY CKEIPALDPQ LLDWLLLEDS           34

PCLEFETEHG FVYRENNKSP GYYDGSTGPC GSCLCLGALM QPKCWLRFKR          146
MTKRFEQQGK TVSVTMIREG FVEQNEIPEE LPLLPKESRY WLREILLCAD          146
MTKRFEQQGK TVSVTMIREG FVEQNEIPEE LPLLPKESRY WLREILLCAD          150
MTKRFEQQGK TVSVTMIREG FVEQNEIPEE LPLLPKESRY WLREILLCAD           84

LKRHTHKHGS ESLDSTMCVK CSVSVSLPTS QKAT...... .........          180
GEPWLAGRTV VPVSTLSGPE LALQKLGKTP LGRYLFTSST LTRDFIEIGR          196
GEPWLAGRTV VPVSTLSGPE LALQKLGKTP LGRYLFTSST LTRDFIEIGR          200
GEPWLAGRTV VPVSTLSGPE LALQKLGKTP LGRYLFTSST LTRDFIEIGR          134

.......... .......... .......... .......... ..........
DAGLWGRRSR LRLSGKPLLL TELFLPASPL Y                              227
DAGLWGRRSR LRLSGKPLLL TELFLPASPL Y                              231
DAGLWGRRSR LRLSGKPLLL TELFLPASPL Y                              165
```

FIG. 1

SEQUENCE LISTING

<160> NUMBER OF SEQ ID NOS: 16

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence:PRIMER

<400> SEQUENCE: 1
ctactcattt catatgtcac accccgcgtt aa                                     32

<210> SEQ ID NO 2
<211> LENGTH: 34
<212> TYPE: DNA
<213> ORGANISM: Artificial Sequence
<220> FEATURE:

-continued

<223> OTHER INFORMATION: Description of Artificial Sequence:PRIMER

<400> SEQUENCE: 2
catcttacta gatctttagt acaacggtga cgcc      34

<210> SEQ ID NO 3
<211> LENGTH: 495
<212> TYPE: DNA
<213> ORGANISM: Unknown Organism
<220> FEATURE:
<223> OTHER INFORMATION: Description of Unknown Organism:E. coli

<400> SEQUENCE: 3
atgtcacacc ccgcgttaac gcaactgcgt gcgctgcgct attgtaaaga gatccctgcc      60
ctggatccgc aactgctcga ctggctgttg ctggaggatt ccatgacaaa acgttttgaa     120
cagcagggaa aaacggtaag cgtgacgatg atccgcgaag ggtttgtcga gcagaatgaa     180
atccccgaag aactgccgct gctgccgaaa gagtctcgtt actggttacg tgaaattttg     240
ttatgtgccg atggtgaacc gtggcttgcc ggtcgtaccg tcgttcctgt gtcaacgtta     300
agcgggccgg agctggcgtt acaaaaattg ggtaaaacgc cgttaggacg ctatctgttc     360
acatcatcga cattaacccg ggactttatt gagataggcc gtgatgccgg gctgtggggg     420
cgacgttccc gcctgcgatt aagcggtaaa ccgctgttgc taacagaact gttttaccg      480 gcgtcaccgt tgtac                                                      495

<210> SEQ ID NO 4
<211> LENGTH: 165
<212> TYPE: PRT
<213> ORGANISM: Unknown Organism
<220> FEATURE:
<223> OTHER INFORMATION: Description of Unknown Organism:E. coli

<400> SEQUENCE: 4

Met Ser His Pro Ala Leu Thr Gln Leu Arg Ala Leu Arg Tyr Cys Lys
 1               5                  10                  15

Glu Ile Pro Ala Leu Asp Pro Gln Leu Leu Asp Trp Leu Leu Leu Glu
            20                  25                  30

Asp Ser Met Thr Lys Arg Phe Glu Gln Gln Gly Lys Thr Val Ser Val
        35                  40                  45

Thr Met Ile Arg Glu Gly Phe Val Glu Gln Asn Glu Ile Pro Glu Glu
    50                  55                  60

Leu Pro Leu Leu Pro Lys Glu Ser Arg Tyr Trp Leu Arg Glu Ile Leu
65                  70                  75                  80

Leu Cys Ala Asp Gly Glu Pro Trp Leu Ala Gly Arg Thr Val Val Pro
                85                  90                  95

Val Ser Thr Leu Ser Gly Pro Glu Leu Ala Leu Gln Lys Leu Gly Lys
            100                 105                 110

Thr Pro Leu Gly Arg Tyr Leu Phe Thr Ser Ser Thr Leu Thr Arg Asp
        115                 120                 125

Phe Ile Glu Ile Gly Arg Asp Ala Gly Leu Trp Gly Arg Arg Ser Arg
    130                 135                 140

Leu Arg Leu Ser Gly Lys Pro Leu Leu Leu Thr Glu Leu Phe Leu Pro
145                 150                 155                 160

Ala Ser Pro Leu Tyr
                165

<210> SEQ ID NO 5

```
<211> LENGTH: 39
<212> TYPE: DNA
<213> ORGANISM: Artificial Sequence
<220> FEATURE:
<223> OTHER INFORMATION: Description of Artificial Sequence:primer

<400> SEQUENCE: 5
ctactcactt agatctccat ggcttcctct gtcatttct                              39

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 6
catcttactc atatgccaca cctgcatgca gc                                    32

<210> SEQ ID NO 7
<211> LENGTH: 684
<212> TYPE: DNA
<213> ORGANISM: Artificial Sequence
<220> FEATURE:
<223> OTHER INFORMATION: Description of Artificial Sequence:synthetic
      CPL

<400> SEQUENCE: 7
atggcttcct ctgtcatttc ttcagcagct gttgccacac gcagcaatgt tacacaagct      60
agcatggttg cacctttcac tggtctcaaa tcttcagcca cttccctgt tacaaagaag      120 caaaaccttg acatcacttc cattgctagc aatggtggaa gagttagctg catgcaggtg    180
tggcatatgt cacacccgc gttaacgcaa ctgcgtgcgc tgcgctattg taagagatc      240 cctgccctgg atccgcaact gctcgactgg ctgttgctgg aggattccat gacaaaacgt    300
tttgaacagc agggaaaaac ggtaagcgtg acgatgatcc gcgaagggtt tgtcgagcag    360
aatgaaatcc ccgaagaact gccgctgctg ccgaaagagt ctcgttactg gttacgtgaa    420
attttgttat gtgccgatgg tgaaccgtgg cttgccggtc gtaccgtcgt tcctgtgtca    480
acgttaagcg gccggagct ggcgttacaa aaattgggta aaacgccgtt aggacgctat    540
ctgttcacat catcgacatt aacccgggac tttattgaga taggccgtga tgccgggctg    600
tgggggcgac gttcccgcct gcgattaagc ggtaaaccgc tgttgctaac agaactgttt    660
ttaccggcgt caccgttgta ctaa                                            684

<210> SEQ ID NO 8
<211> LENGTH: 227
<212> TYPE: PRT
<213> ORGANISM: Artificial Sequence
<220> FEATURE:
<223> OTHER INFORMATION: Description of Artificial Sequence:synthetic
      CPL

<400> SEQUENCE: 8

Met ala Ser Ser Val Ile Ser Ser Ala Ala Val Ala Thr Arg Ser Asn
 1               5                  10                  15

Val Thr Gln Ala Ser Met Val Ala Pro Phe Thr Gly Leu Lys Ser Ser
            20                  25                  30

Ala Thr Phe Pro Val Thr Lys Lys Gln Asn Leu Asp Ile Thr Ser Ile
        35                  40                  45

Ala Ser Asn Gly Gly Arg Val Ser Cys Met Gln Val Trp His Met Ser
    50                  55                  60
```

```
His Pro Ala Leu Thr Gln Leu Arg Ala Leu Arg Tyr Cys Lys Glu Ile
 65                  70                  75                  80

Pro Ala Leu Asp Pro Gln Leu Leu Asp Trp Leu Leu Leu Glu Asp Ser
                 85                  90                  95

Met Thr Lys Arg Phe Glu Gln Gln Gly Lys Thr Val Ser Val Thr Met
            100                 105                 110

Ile Arg Glu Gly Phe Val Glu Gln Asn Glu Ile Pro Glu Glu Leu Pro
        115                 120                 125

Leu Leu Pro Lys Glu Ser Arg Tyr Trp Leu Arg Glu Ile Leu Leu Cys
    130                 135                 140

Ala Asp Gly Glu Pro Trp Leu Ala Gly Arg Thr Val Pro Val Ser
145                 150                 155                 160

Thr Leu Ser Gly Pro Glu Leu Ala Leu Gln Lys Leu Gly Lys Thr Pro
                165                 170                 175

Leu Gly Arg Tyr Leu Phe Thr Ser Ser Thr Leu Thr Arg Asp Phe Ile
            180                 185                 190

Glu Ile Gly Arg Asp Ala Gly Leu Trp Gly Arg Ser Arg Leu Arg
        195                 200                 205

Leu Ser Gly Lys Pro Leu Leu Leu Thr Glu Leu Phe Leu Pro Ala Ser
    210                 215                 220

Pro Leu Tyr
225

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 9
ctactcattt gaagactgca tgcaggtgtg gcat                              34

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 10
catcttactg tcgactttag tacaacggtg acgc                              34

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 11
ctactcattt ggccagctct gtcatttctt cagcagc                           37

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 12
```

```
catcttacta gatctttagt acaacggtga c                                    31

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 13
cccgggggta cctaaagaag gagtgcgtcg aag                                  33

<210> SEQ ID NO 14
<211> LENGTH: 46
<212> TYPE: DNA
<213> ORGANISM: Artificial Sequence
<220> FEATURE:
<223> OTHER INFORMATION: Description of Artificial Sequence:primer

<400> SEQUENCE: 14
gatatcaagc tttctagagt cgacatcgat ctagtaacat agatga                    46

<210> SEQ ID NO 15
<211> LENGTH: 62
<212> TYPE: PRT
<213> ORGANISM: Artificial Sequence
<220> FEATURE:
<223> OTHER INFORMATION: Description of Artificial Sequence:synthetic
      CPL

<400> SEQUENCE: 15

Met Ala Ser Ser Val Ile Ser Ser Ala Ala Val Ala Thr Arg Ser Asn
  1               5                  10                  15

Val Thr Gln Ala Ser Met Val Ala Pro Phe Thr Gly Leu Lys Ser Ser
             20                  25                  30

Ala Thr Phe Pro Val Thr Lys Lys Gln Asn Leu Asp Ile Thr Ser Ile
         35                  40                  45

Ala Ser Asn Gly Gly Arg Val Ser Cys Met Gln Val Trp His
     50                  55                  60

<210> SEQ ID NO 16
<211> LENGTH: 170
<212> TYPE: PRT
<213> ORGANISM: Artificial Sequence
<220> FEATURE:
<223> OTHER INFORMATION: Description of Artificial Sequence:synthetic
      CPL

<400> SEQUENCE: 16

Met Gln Val Trp His Met Ser His Pro Ala Leu Thr Gln Leu Arg Ala
  1               5                  10                  15

Leu Arg Tyr Cys Lys Glu Ile Pro Ala Leu Asp Pro Gln Leu Leu Asp
             20                  25                  30

Trp Leu Leu Leu Glu Asp Ser Met Thr Lys Arg Phe Glu Gln Gln Gly
         35                  40                  45

Lys Thr Val Ser Val Thr Met Ile Arg Glu Gly Phe Val Glu Gln Asn
     50                  55                  60

Glu Ile Pro Glu Glu Leu Pro Leu Leu Pro Lys Glu Ser Arg Tyr Trp
 65                  70                  75                  80

Leu Arg Glu Ile Leu Leu Cys Ala Asp Gly Glu Pro Trp Leu Ala Gly
             85                  90                  95
```

```
                            -continued

Arg Thr Val Val Pro Val Ser Thr Leu Ser Gly Pro Glu Leu Ala Leu
            100             105             110

Gln Lys Leu Gly Lys Thr Pro Leu Gly Arg Tyr Leu Phe Thr Ser Ser
        115             120             125

Thr Leu Thr Arg Asp Phe Ile Glu Ile Gly Arg Asp Ala Gly Leu Trp
    130             135             140

Gly Arg Arg Ser Arg Leu Arg Leu Ser Gly Lys Pro Leu Leu Leu Thr
145             150             155             160

Glu Leu Phe Leu Pro Ala Ser Pro Leu Tyr
                165             170
```

HIGH LEVEL PRODUCTION OF P-HYDROXYBENZOIC ACID IN GREEN PLANTS

This application claims the benefit of U.S. Provisional Application No. 60/209,854, filed Jun. 2, 2000.

FIELD OF THE INVENTION

The invention relates to the field of plant gene expression and molecular biology and microbiology. More specifically, a method is presented for the production of p-hydroxybenzoic acid (pHBA) in green plants which relies on the expression of a unique expression cassette comprising a gene encoding chorismate pyruvate lyase operably linked to a specific chloroplast targeting sequence.

BACKGROUND OF THE INVENTION p-Hydroxybenzoic acid (pHBA) is the major monomeric component (~65% by weight) of Zenite™, a Liquid Crystal Polymer (LCP). LCP's have superior properties over conventional resins such as high strength/stiffness, low melt viscosity, excellent environmental resistance, property retention at elevated temperatures, and low gas permeability. However, current synthetic methods for the synthesis of pHBA (Kolbe-Schmitt reaction (Kolbe and Lautemann, *Ann.* 113:125 (1869)), are prohibitively expensive, and an inexpensive route to LCP monomers would open up many new applications for their use in the automotive, electrical, and other industries. Biological production offers one potential, less expensive route to pHBA production.

pHBA has been produced in microbial systems. For example, JP 06078780 teaches pHBA preparation by culturing benzoic acid in the presence of microorganisms (preferably Aspergillus) that oxidize benzoic acid to pHBA. Additionally, strains of Enterobacter with the ability to convert p-cresol to pHBA have been isolated from soil (JP 05328981). Further, JP 05336980 and JP 05336979 disclose isolated strains of *Pseudomonas putida* with the ability to produce pHBA from p-cresol. Similarly, commonly owned WO 9856920 teaches a method for the production of pHBA from toluene using a *Pseudomonas mendocina* mutant lacking the ability to express para-hydroxybenzoate hydroxylase (pHBH). Finally, U.S. Pat. No. 6,030,819 teaches the production of pHBA in genetically engineered *E. coli* expressing the chorismate pyruvate lyase (CPL) gene.

In spite of these successes the ability to produce commercially useful quantities of pHBA in microbial platforms is hampered by the use of toxic starting materials and limited biomass. A method for pHBA production that overcomes these problems is needed.

Coincidentally, pHBA is naturally occurring in nearly all plants, animals, and, microorganisms, albeit in miniscule quantities. In many bacteria, the generation of pHBA occurs by way of chorismate, an important branchpoint intermediate in the synthesis of numerous aromatic compounds, including phenylalanine, tyrosine, p-aminobenzoic acid, and ubiquinone. In *E. coli*, chorismate itself undergoes five different enzymatic reactions to yield five different products, and the enzyme that is ultimately responsible for the synthesis of pHBA is chorismate pyruvate lyase, which is known as CPL. The latter is the product of the *E. coil* ubiC gene, which was independently cloned by two different groups (Siebert et al., *FEBS Lett* 307:347–350 (1992); Nichlols et al., *J. Bacteriol* 174:5309–5316 (1992)). The enzyme is a 19 kDa monomeric protein with no known co-factors or energy requirements. Through elimination of the $C_3$ enolpyruvyl side chain of its sole substrate, CPL catalyzes the direct conversion of 1 mol of chorismate to 1 mol of pyruvate and 1 mol of pHBA. Recombinant CPL has been overexpressed in *E. coli*, purified to homogeneity, and partially characterized both biochemically and kinetically (Siebert et al., *Microbiology* 140:897–904; Nichlols et al., *J. Bacteriol* 174:5309–5316 (1992)). In addition a detailed mechanism for the CPL enzyme reaction has also been proposed (Walsh et al., *Chem Rev.* 90:1105–1129).

In plants pHBA has been found in carrot tissue (Schnitzler et al., *Planta,* 188, 594, (1992)), in a variety of grasses and crop plants (Lydon et al., (*J. Agric. Food. Chem.,* 36, 813, (1988), in the lignin of poplar trees (Terashima et al., *Phytochemistry,* 14, 1991, (1972); and in a number of other plant tissues (Billek et al., *Oesterr. Chem.,* 67, 401, (1966). The fact that plants possess all of the necessary enzymatic machinery to synthesize pHBA suggests that they may be a useful platform for the production of this monomer. For example, as a renewable resource a plant platform would require far less energy and material consumption than either petrochemical or microbial methods. Similarly, a plant platform represents a far greater available biomass for monomer production than a microbial system. Finally, the natural presence of pHBA in plants suggests that host toxicity as a result of overproduction of the compound might not be a problem. Nevertheless, in spite of the obvious benefits of using plants as a means to produce pHBA, high level production of the monomer has been elusive.

One difficulty to be overcome lies in the metabolic fate of chorismate in plant tissues. Indeed, the production of pHBA from chorismate is vastly more complicated in higher plants than microbes, since the former lack an enzyme that is functionally equivalent to CPL. For example, the biosynthetic pathway leading to pHBA in *Lithospermum erythrorhizon* is thought to consist of up to 10 successive reactions (Loscher and Heide, *Plant Physiol.* 106:271–279 (1992)), presumably all catalyzed by different enzymes. Moreover, most of the enzymes that catalyze these reactions have not been identified, nor have their genes been cloned. Even less information is available on how pHBA is synthesized in other plant species. To further complicate matters, those enzymes that are known to participate in plant pHBA production span two different pathways, that are differentially regulated and located in different cellular compartments. Thus, chorismate is an intermediate of the shikimate pathway which is largely confined to chloroplasts and other types of plastids (Siebert et al., *Plant Physiol.* 112:811–819 (1996)) Sommer et al., *Plant Cell Physiol.* 39(11): 1240–1244 (1998)), while all of the intermediates downstream from phenylalanine belong to the phenylpropanoid pathway which takes place in both the cytosol and endoplasmic reticulum.

Despite the lack of understanding of how plants normally synthesize pHBA and the enzymes that are involved in this process, transgenic plants that accumulate significantly higher levels of pHBA than wildtype plants have been described. For example, Kazufumi Yazaki, (*Baiosaiensu to Indasutori* (1998), 56(9), 621–622) discusses the introduction of the CPL encoding gene into tobacco for the production of pHBA in amounts sufficient to confer insect resistance. Similarly, Siebert et al., (*Plant Physiol.* 112:811–819 (1996)) have demonstrated that tobacco plants (*Nicotiana tabacum*) transformed with a constitutively expressed chloroplast-targeted version of *E. coli* CPL (referred to as "TP-UbiC") have elevated levels of pHBA that are at least three orders of magnitude greater than wildtype plants (WO 96/00788 granting as DE 4423022). Interestingly, the genetically modified tobacco plants contained only trace amounts of free pHBA. Instead, virtually all of the compound (~98%) was converted to two glucose conjugates, a phenolic glucoside and an ester glucoside, that were present in a ratio of about 3:1 (Siebert et al., *Plant Physiol* 112:811–819 (1996); Li et al., *Plant Cell Physiol.* 38(7):844–850 (1997)). Both glucose conjugates were 1-β-D-glucosides, with a single glucose residue covalently attached to the hydroxyl or carboxyl group of pHBA. The best transgenic plant that was identified in this study had a total pHBA glucoside content of 0.52% of dry weight, when leaf tissue was analyzed. Correcting for the associated glucose residue, the actual amount of pHBA that was produced in the transgenic tobacco plants was only about half of this value.

In more recent studies, the same artificial fusion protein was expressed in transformed tobacco cell cultures using both a constitutive promoter (Sommer et al., *Plant Cell Physiol.* 39(11):1240–1244 (1998)) and an inducible promoter (Sommer et al., *Plant Cell Reports* 17:891–896 (1998)). While the accumulation of pHBA glucosides was slightly higher than the original study with whole plants, in neither case did the levels exceed 0.7% of dry weight. In contrast, when TP-UbiC was examined in hairy root cultures of *Lithospermum erythrorhizon* (Sommer et al., *Plant Molecular Biology* 39:683–693 (1999)) the pHBA glucoside content reached levels as high as 0.8% of dry weight, after correcting for the endogenous levels in the untransformed control cultures.

Although these studies demonstrate the feasibility of using genetic engineering to increase the level of pHBA in higher plants, the TP-UbiC artificial fusion protein described above is unable to generate the compound in commercially useful quantities. Such an effort will require increasing the pHBA content of an agronomically suitable plant to levels that are 10- to 20-fold higher than those previously reported. Thus, one or more modifications of the present systems are needed to achieve these levels. Since chorismate, the substrate for CPL, is synthesised in plastids, one potential area for improvement may lie in the design of a better chloroplast targeting sequence to achieve higher levels of enzyme activity in the cellular compartment of interest. Indeed, that there is a positive correlation between CPL enzyme activity and accumulation of pHBA glucosides is apparent in several of the studies noted above (Siebert et al., *Plant Physiol.* 112:811–819 (1996); Sommer et al., *Plant Cell Physiol.* 39(11):1240–1244 (1998); Sommer et al *Plant Cell Reports* 17:891–896 (1998)). Furthermore, in none of these studies is there any evidence to suggest that the systems were saturated with CPL enzyme activity using the TP-UbiC artificial fusion protein.

It is well known that most naturally occurring chloroplast proteins are nuclear-encoded and synthesized as larger molecular weight precursors with a cleavable N-terminal polypeptide extension called a transit peptide. It is also generally accepted that the latter contains all of the information that is necessary for translocation into the chloroplast. Although the mechanistic details of protein import remain to be elucidated, several important facts have emerged: (a) precursor uptake occurs post-translationally (Chua and Schmidt, *Proc Natl. Acad. Sci.* 75:6110–6114 (1978); Highfield and Ellis, *Nature* 271:420–424 (1978)) and is mediated by proteinacious receptors that exist in the chloroplast envelope membranes (Cline et al.,*J. Biol. Chem.* 260:3691–3696 (1985))); (b) ATP-hydrolysis is the sole driving force for translocation (Grossman et al., *Nature* 285:625–628 (1980); Cline et al., *J. Biol. Chem.* 260:3691–3696 (1985)); (c) fusion of a transit peptide to a foreign protein is at times, but not always, sufficient to trigger uptake into chloroplasts, both in vivo ((Van den Broeck et al., *Nature* 313:358–362 (1985)); Schreier et al., *EMBO J.* 4:25–32 (1985)) and in vitro Wasmann et al., *Mol. Gen. Genet.* 205:446–453 (1986)); and finally, (d) following chloroplast import, the transit peptide is proteolytically removed from the precursor protein to give rise to the "mature" polypeptide. Although the complete sequence of thousands of transit peptides are now known, the manipulation of these sequences to achieve optimal targeting and expression of foreign proteins in the chloroplast compartment of plants is still a matter of trial and error. It is well settled however, that simply attaching a transit peptide to a foreign protein does not necessarily guarantee that it will be efficiently taken up by chloroplasts or properly processed. Even when the same targeting sequence is fused to different proteins, the results are completely unpredictable (Lubben et al., *The Plant Cell* 1:1223–1230 (1989)), and the different passenger proteins are transported with different efficiencies. The reasons for this are not clear, however it has been suggested that chloroplast uptake and removal of the transit peptide are somehow coupled, and that certain artificial fusion proteins are either not processed or processed ineffectively. For example, it has been shown that even very subtle changes in the vicinity of the natural cleavage site of the Rubisco small subunit precursor can lead to aberrant processing (Robinson and Ellis, *Eur. J. Biochem.* 142:342–346 (1984); Robinson and Ellis, *Eur. J. Biochem.* 152:67–73 (1985)) and diminished chloroplast uptake (Wasmann et al., *J. Biol. Chem.* 263:617–619 (1988)).

Some degree of improvement has been achieved in this area by including in the chloroplast targeting sequence not only the transit peptide and the scissile bond, but also a small portion of the mature N-terminus of the transit peptide donor. Indeed, this approach has worked both in vivo and in vitro ((Van den Broeck et al., *Nature* 313:358–362 (1985); Schreier et al., *EMBO J.* 4:25–32 (1985); Wasmann et al., *Mol. Gen. Genet.* 205:446–453 (1986); Herrera-Estrella et al., EP 0189707; U.S. Pat. No. 5,728,925; U.S. Pat. No. 5,717,084) for another bacterial protein, namely, neomycin phosphotransferase II (NPT-II). Thus, a chimeric protein consisting of the transit peptide of the Rubisco small subunit precursor plus the first 22 residues of mature Rubisco fused to the N-terminus of NPT-II was taken up by chloroplasts much better than a similar construct that only contained the transit peptide and scissile bond. This strategy is not foolproof however, and is still associated with a high degree of unpredictability that is inextricably linked to the passenger protein. This is most readily seen in the literature attempts to target CPL to chloroplasts. For example Sommer et al., *Plant Cell Physiol.* 39(11):1240–1244 (1998)) describes an analogous artificial fusion protein comprising the CPL gene product fused at its N-terminus to the transit peptide and first 21 amino acid residues of the Rubisco small subunit (e.g., "TP21UbiC"). While it was anticipated that this modification would improve chloroplast uptake and processing, the cells that contained the original construct, TP-UbiC, had much higher levels of both CPL enzyme activity and pHBA glucosides. Thus, application of the teaching of Wasmann et al., (*Mol. Gen. Genet.* 205:446–453 (1986)) had a detrimental effect on a different protein.

The problem to be solved therefore is to provide a method for the production of pHBA in plants at commercially useful levels taking advantage of the chemical reaction that is catalyzed by the bacterial protein CPL. This is a particularly ambitious goal since on top of all of the complications noted above it is clear from the literature that certain N-terminal modifications of *E. coli* CPL can result in a substantial loss of enzyme activity (Siebert et al., *Plant Physiol.* 112:811–819 (1996). Consequently, it is not only essential to identify an artificial fusion protein that is efficiently imported into chloroplasts, but one that is also proteolytically processed to yield either unmodified CPL or a CPL variant with an N-terminal extension that doesn't interfere with enzyme activity. The solution to this problem is not taught in the art. Applicant has solved the stated problem by creating a novel artificial fusion protein that enables the expression of sufficiently high levels of CPL enzyme activity in chloroplasts to accumulate commercially useful levels of pHBA.

SUMMARY OF THE INVENTION

The present invention provides a method for the production of pHBA in a green plant comprising:
a) providing a green plant having an endogenous source of chorismate and containing a chorismate pyruvate lyase expression cassette having the following structure:

P-T-C-D-CPL wherein:
P is a promoter suitable for driving the expression of a chorismate pyruvate lyase gene;
T is a nucleic acid molecule encoding a rubisco chloroplast transit peptide;
C a nucleic acid molecule encoding a Rubisco chloroplast transit peptide cleavage site;
D is a nucleic acid molecule encoding from about 4 to about 20 contiguous amino acids of the N-terminal portion of a Rubisco chloroplast transit peptide donor polypeptide; and
CPL is a nucleic acid molecule encoding a mature chorismate pyruvate lyase protein;
wherein each of P, T, C, D, and CPL are operably linked such that expression of the cassette results in translation of a chimeric protein comprising a chloroplast targeting sequence fused to the N-terminus of the mature chorismate pyruvate lyase protein;
b) growing said plant under conditions whereby the chimeric protein is expressed and translocated to the chloroplast for the conversion of chorismate to para-hydroxy benzoic acid glucoside and para-hydroxy benzoic acid derivatives;
c) recovering para-hydroxy benzoic acid and para-hydroxy benzoic acid derivatives from the plant; and
d) processing said the para-hydroxy benzoic acid glucoside and para-hydroxy benzoic acid derivatives to free para-hydroxy benzoic acid.

Specifically, the present method produces para-hydroxy benzoic acid glucosides in plants at a concentration of greater than 2% of the dry weight of the plant biomass and preferably at a concentration of greater than 10%.

Additionally the invention provides a chorismate pyruvate lyase expression cassette comprising: a chimeric gene having a nucleic acid molecule encoding a ribulose-1,5-bisphosphate carboxylase small subunit derived chloroplast targeting sequence having an amino acid sequence as set forth in SEQ ID NO:15 operably linked to a nucleic acid molecule encoding a chorismate pyruvate lyase enzyme having the amino acid sequence as set forth in SEQ ID NO:4.

BRIEF DESCRIPTION OF THE DRAWINGS SEQUENCE DESCRIPTIONS

FIG. 1 shows a primary amino acid sequence alignment of two different chloroplast-targeted versions of CPL. Both are artificial fusion proteins. The one in line 3 corresponds to TP-UbiC which was used in previous studies (Siebert et al., *Plant Physiol.* 112:811–819 (1996) Sommer et al., *Plant Cell Physiol.* 39(11):1240–1244 (1998); Sommer et al., *Plant Cell Reports* 17:891–896 (1998); Sommer et al., *Plant Molecular Biology* 39:683–693 (1999)), while the one in line 2 corresponds to TP-CPL which was developed in the present work. *E. coli* CPL (line 4) and the tomato Rubisco small subunit precursor for rbcS2 (line 1) are also included in the alignment. Amino acid residues corresponding to the "mature" Rubisco small subunit are indicated in bold. The N-terminal chloroplast transit peptide of the Rubisco small subunit precursor is indicated in plain text. The primary amino acid sequence of *E. coli* CPL is indicated in italics. The arrow indicates the highly conserved Cys-Met junction (Mazur et al., *Nuc Acids Res.* 13:2373–2386 (1985); Berry-Lowe et al., *J. Mol. and Appl. Gen.* 1, 483–498 (1982)) where transit peptide cleavage normally occurs to give rise to the mature Rubisco small subunit.

Figure 6:
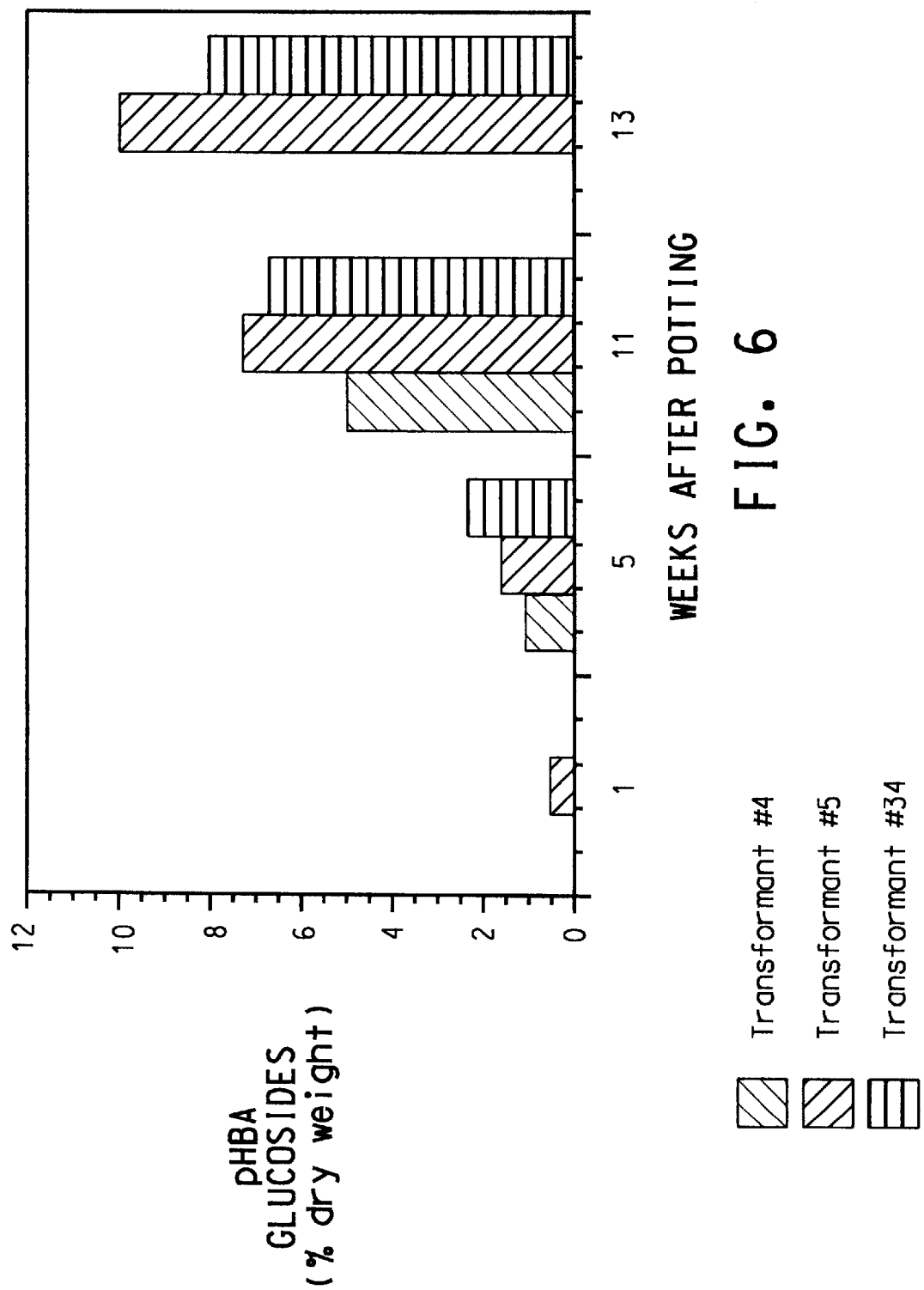

FIG. 6 shows the age-dependent accumulation of total pHBA glucosides in transgenic tobacco plants expressing TP-CPL. The analysis was conducted on leaf tissue that was obtained from primary transformants at various stages of development. Total pHBA glucosides are expressed as a percentage of dry weight.

Figure 7:
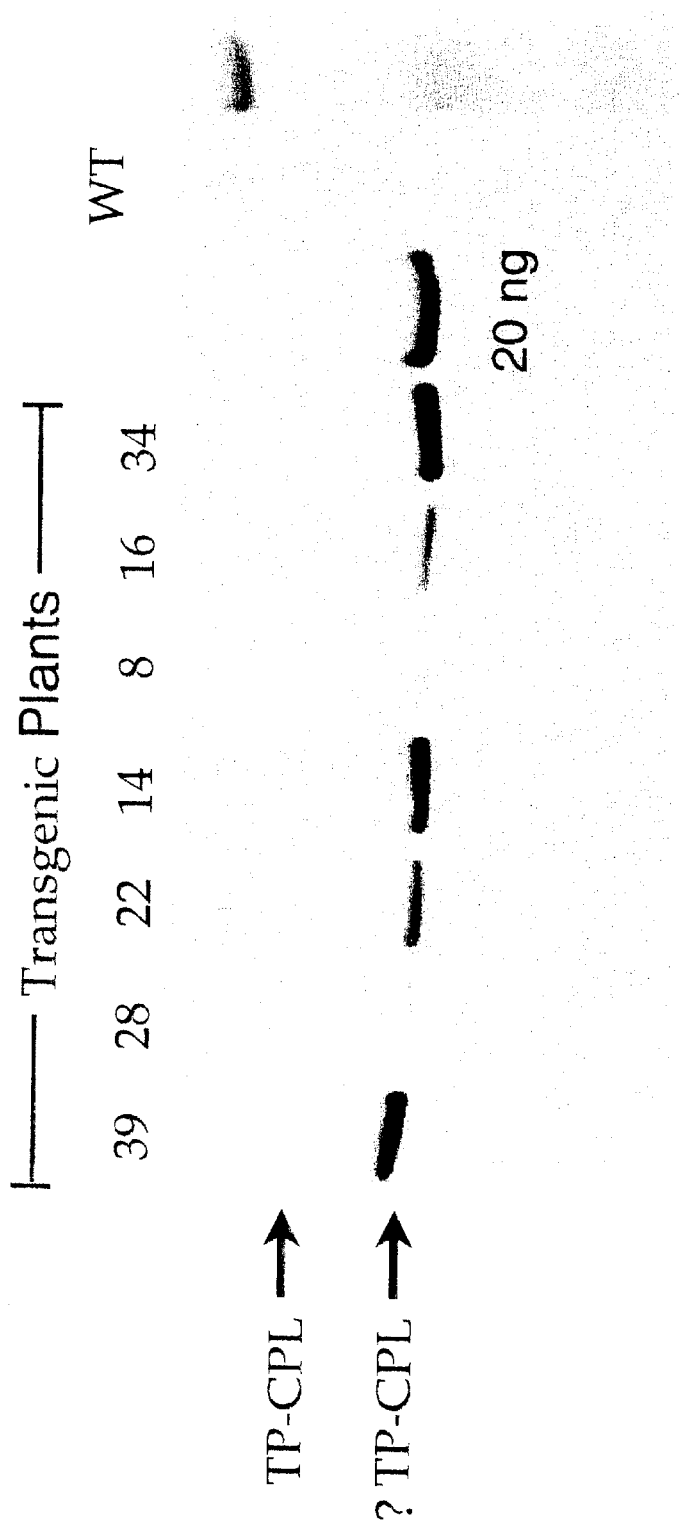

FIG. 7 shows a Western blot of wildtype (lane 9) and transgenic tobacco plants expressing TP-CPL (lanes 1–7). The analysis was conducted on leaf tissue that was obtained from 5-week-old primary transformants. Lane 8 contains 20 ng of purified recombinant ΔTP-CPL (e.g., the predicted chloroplast cleavage product of TP-CPL). Following SDS-PAGE, proteins were transferred to nitrocellulose and probed with a 1:200 dilution of anti-CPL antisera.

The invention can be more fully understood from the following detailed description and the accompanying sequence descriptions which form a part of this application.

Applicant(s) have provided 16 sequences in conformity with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Adminstrative Instructions). The symbols and format used for nucleotide and amino acid sequence data comply with the rules set forth in 37 C.F.R. §1.822.

SEQ ID NO: 1 is the 5' primer useful for introducing *E. coli* CPL, having Genbank accession No. M96268, into the *E. coli* expression vector, pET-24a (+) (Novagen).

SEQ ID NO:2 is the 3' primer useful for introducing *E. coli* CPL, having Genbank accession No. M96268, into the *E. coli* expression vector, pET-24a (+) (Novagen).

SEQ ID NO:3 is the nucleotide sequence of the ORF of *E. coli* CPL, having Genbank accession No. M96268, in the *E. coli* expression vector, pET-24a (+) (Novagen).

SEQ ID NO:4 is the primary amino acid sequence of the ORF of *E. coli* CPL, having Genbank accession No. M96268, in the *E. coli* expression vector, pET-24a (+) (Novagen).

SEQ ID NO:5 is the 5' primer useful for the amplification of the chloroplast targeting sequence of the tomato Rubisco small subunit precursor, for expression of TP-CPL in *E. coli*.

SEQ ID NO:6 is the 3' primer useful for the amplification of the chloroplast targeting sequence of the tomato Rubisco small subunit precursor, for expression of TP-CPL in *E. coli*.

SEQ ID NO:7 is the nucleotide sequence of the ORF of the chloroplast-targeted CPL fusion protein (TP-CPL) in the *E. coli* expression vector, pET-24a (+) Novagen).

SEQ ID NO:8 is the primary amino acid sequence of the ORF of the chloroplast-targeted CPL fusion protein (TP-CPL) in the *E. coli* expression vector, pET-24a (+) (Novagen).

SEQ ID NO:9 is the 5' primer useful for the amplification of the predicted chloroplast cleavage product of TP-CPL (ATP-CPL), and its insertion into the *E. coli* expression vector, pET-24d (+) (Novagen).

SEQ ID NO: 10 is the 3' primer useful for the amplification of the predicted chloroplast cleavage product of TP-CPL (ATP-CPL), and its insertion into the *E. coli* expression vector, pET-24d (+) (Novagen).

SEQ ID NO:11 is the 5' primer useful for amplification and modification of TP-CPL, without changing its primary amino acid sequence, for insertion into the in vitro transcription/translation vector, pCITE4a(+) (Novagen).

SEQ ID NO:12 is the 3' primer useful for amplification and modification of TP-CPL, without changing its primary amino acid sequence, for insertion into the in vitro transcription/translation vector, pCITE4a(+) (Novagen).

SEQ ID NO: 13 is the 5' primer useful for the amplification of a truncated version of the 3' NOS terminator sequence using plasmid pMH40 as a template.

SEQ ID NO:14 is the 3' primer useful for the amplification of a truncated version of the 3' NOS terminator sequence using plasmid pMH40 as a template.

SEQ ID NO:15 is the chloroplast-targeting sequence derived from the tomato ribulose-1,5-bisphosphate carboxylase small subunit.

SEQ ID NO: 16 is the processed chloroplast-targeted CPL fusion protein (TP-CPL).

DETAILED DESCRIPTION OF THE INVENTION

The present invention provides methods for the high level of production of para-hydroxy benzoic acid (pHBA) in green plants at commercially useful levels. pHBA is useful as a monomer in liquid crystalline polymers which have application in the automotive, electrical, and other industries.

The method relies on the effective expression of a gene encoding a modified version of the enzyme chorismate pyruvate lyase (CPL) which catalyzes the direct conversion of 1 mol of chorismate to 1 mol of pyruvate and 1 mol of pHBA. The CPL variant is introduced into a green plant in the form of an expression cassette which comprises the CPL coding sequence operably linked to a suitable promoter capable of driving protein expression in plants. Additionally the expression cassette contains a DNA fragment that is situated directly upstream and contiguous to the CPL coding sequence which encodes a chloroplast transit peptide, its natural cleavage site, and a small portion of the transit peptide donor polypeptide. The transit peptide functions to target the chimeric protein encoded by the expression cassette to the chloroplast and enables its uptake into the organelle that is responsible for the synthesis of chorismate, the substrate of CPL that is converted to pHBA. The cleavage site is unique to the original transit peptide donor and cleavage of the artificial protein encoded by this cassette at this site liberates a novel polypeptide comprising the mature CPL enzyme that contains at its N-terminus a small portion of the transit peptide donor.

In this disclosure, a number of terms and abbreviations are used. The following definitions are provided.

"Polymerase chain reaction" is abbreviated PCR.

"Chorismate Pyruvate Lyase" is abbreviated CPL and refers to a gene encoding an enzyme which catalyzes the conversion of chorismate to pyruvate and pHBA.

"Para-hydroxybenzoic acid" or "P-hydroxybenzoic acid" is abbreviated pHBA.

The term "P-hydroxybenzoic acid glucoside" or "pHBA glucoside" refers to a conjugate comprising pHBA and a glucose molecule.

The term "pHBA derivative" refers to any conjugate of pHBA that may be formed in a plant as the result of the catalytic activity of the CPL enzyme.

The term "transit peptide" or "chloroplast transit peptide" will be abbreviated "TP" and refers to the N-terminal portion of a chloroplast precursor protein that directs the latter into chloroplasts and is subsequently cleaved off by the chloroplast processing protease.

The term "chloroplast-targeting sequence" refers to any polypeptide extention that is attached to the N-terminus of a foreign protein for the purpose of translocation into the chloroplast. In the case of a naturally occuring chloroplast precursor protein, the transit peptide is considered to be the chloroplast-targeting sequence, although optimal uptake and proteolytic processing may depend in part on portions of the "mature" chloroplast protein.

The term "transit peptide donor sequence" refers to that portion of the chloroplast-targeting sequence that is derived from the "mature" portion of the choroplast precursor protein. The transit peptide donor sequence is always downstream and immediately adjacent to the transit peptide cleavage site that separates the transit peptide from the mature chloroplast protein.

The term "chloroplast processing protease" refers to a protease enzyme capable of cleaving the scissile bond between the transit peptide and the mature chloroplast protein.

The term "transit peptide cleavage site" refers to a site between two amino acids in a chloroplast-targeting sequence at which the chloroplast processing protease acts.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

CPL Expression Cassette

The present invention provides an expression cassette useful for the expression of a fully-active, modified version of chorismate pyruvate lyase (CPL) and the targeting of that polypeptide to the chloroplasts of the host plant. Typically the expression cassette will comprise (1) the cloned CPL gene under the transcriptional control of 5' and 3' regulatory sequences and (2) a dominant selectable marker. The present expression cassette may also contain, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal. In a preferred embodiment the instant cassette will additionally contain sequences encoding a transit peptide as well as sequences encoding a portion of the transit peptide donor which contains a transit peptide cleavage site that is amenable to processing by the host plant cell chloroplast processing protease. Optionally the instant cassette may also comprise one or more introns in order to facilitate CPL expression.

The CPL gene encodes an enzyme which converts 1 mol of chorismate to 1 mol of pyruvate and 1 mol of pHBA. The most well characterized CPL gene has been isolated from *E. coli* and bears the GenBank accession number M96268.

Promoters useful for driving the instant CPL gene are numerous and well known in the art. Suitable promoters will be those that operate in plants and generally will be derived from the plant host in which the CPL expression cassette resides. Any combination of any promoter and any terminator capable of inducing expression of the CPL gene may be used in the present cassette. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequences of the present invention should be capable of promoting expression of the present gene product. High level plant promoters that may be used in this invention include the promoter of the small subunit (ss) of the ribulose-1,5-bisphosphate carboxylase for example from soybean (Berry-Lowe et al., *J. Molecular and App. Gen.*, 1:483–498 1982)), and the promoter of the chlorophyll a/b binding protein. These two promoters are known to be light-induced in plant cells (See, for example, *Genetic Engineering of Plants, an Agricultural Perspective*, A. Cashmore, Plenum, New York (1983), pages 29–38; Coruzzi, G. et al., *The Journal of Biological Chemistry*, 258:1399 (1983), and Dunsmuir, P. et al., *Journal of Molecular and Applied Genetics*, 2:285 (1983)).

In the present invention where polypeptide expression is desired, it is generally desirable to include a polyadenylation region at the 3'-end of a CPL coding region. The polyadenylation region can be derived a variety of plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8:4395–4405 (1988); Callis et al., *Genes Dev.* 1:1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

In a preferred embodiment it will be useful to direct the CPL protein to the chloroplast and other plastids. Typically this is effected by the introduction of a chloroplast transit peptide which targets the expressed protein to plastids and also facilitates its translocation into the organelle. A number of chloroplast transit peptides are known and could be used in the present expression cassette, including but not limited to those derived from Pisum (Esutorera et al., JP 1986224990; E00977), carrot (Luo et al, *Plant Mol. Biol.*, 33 (4), 709–722 (1997;Z33383), Nicotiana (Bowler et al., EP 0359617; A09029), Oryza (de Pater et al., *Plant Mol. Biol.*, 15 (3), 399–406 (1990); X51911, as well as synthetic sequences such as those provided in Herrera-Estrella et al., EP 0189707; U.S. Pat. No. 5,728,925; U.S. Pat. No. 5,717,084 (A10396 and A10398). Preferred in the present invention is the chloroplast transit peptide of the ribulose-1,5-bisphosphate carboxylase (Rubisco) small subunit precursor protein isolated from any plant. The Rubisco small subunit is well characterized from a variety of plants and the transit peptide from any of them will be suitable for use in the present invention. See for example Physcomitrella (Quatrano et al., AW599738); Lotus (Poulsen et al., AW428760); Citrullus (J. S. Shin, AI563240); Nicotiana (Appleby et al., Heredity (1997), 79(6), 557–563); alfalfa (Khoudi et al., *Gene* (1997), 197(1/2), 343–351); potato and tomato (Fritz et al., *Gene* (1993), 137(2), 271–4); wheat (Galili et al., *Theor. Appl. Genet.* (1991), 81(1), 98–104); and rice (Xie et al., *Sci. Sin., Ser. B* (Engl. Ed.) (1987), 30(7), 706–19). For example, transit peptides may be derived from the Rubisco small subunit isolated from plants including but not limited to, soybean, rapeseed, sunflower, cotton, corn, tobacco, alfalfa, wheat, barley, oats, sorghum, rice, Arabidopsis, sugar beet, sugar cane, canola, millet, beans, peas, rye, flax, and forage grasses. Preferred for use in the present invention is the tomato Rubisco small subunit precursor protein.

Chloroplast targeting sequences not only target the desired protein to the chloroplast but also facilitates its translocation into the organelle. This is accompanied by the cleavage of the transit peptide from the mature polypeptide or protein at the appropriate transit peptide cleavage site by a chloroplast processing protease, native to the chloroplast. Accordingly the present chloroplast targeting sequence comprises a suitable cleavage site for the correct processing of the pre-protein to an active mature polypeptide contained within the chloroplast. Preferred in the present invention is the chloroplast targeting sequence of the tomato Rubisco small subunit precursor protein having a cleavage site between the naturally occurring Cys and Met residues that separate the transit peptide from the mature polypeptide.

The functional CPL expression cassette is used to transform a suitable plant host for the expression of CPL and the production of pHBA glucoside in the chloroplast. Virtually any plant host that is capable of supporting the expression of the CPL gene will be suitable, however crop plants are preferred for their ease of harvesting and large biomass. Suitable plant hosts will include but are not limited to both monocots and dicots such as soybean, rapeseed (*Brassica napus, B. campestris*), sunflower (*Helianthus annus*), cotton (*Gossypium hirsutum*), corn, tobacco (*Nicotiana tabacum*), alfalfa (*Medicago sativa*), wheat (*Triticum sp*), barley (*Hordeum vulgare*), oats (*Avena sativa*, L), sorghum (*Sorghum bicolor*), rice (*Oryza sativa*), Arabidopsis, sugar beet, sugar cane, canola, millet, beans, peas, rye, flax, and forage grasses.

A variety of techniques are available and known to those skilled in the art for introduction of constructs into a plant cell host. These techniques include transformation with DNA employing *A. tumefaciens* or *A. rhizogenes* as the transforming agent, electroporation, particle acceleration, etc. [See for example, EP 295959 and EP 138341]. One suitable method involves the use of binary type vectors of Ti and Ri plasmids of Agrobacterium spp. Ti-derived vectors transform a wide variety of higher plants, including monocotyledonous and dicotyledonous plants, such as soybean, cotton, rape, tobacco, and rice [Pacciotti et al. (1985) *Bio/Technology* 3:241; Byrne et al., (1987) *Plant Cell, Tissue and Organ Culture* 8:3; Sukhapinda et al., (1987) *Plant Mol. Biol.* 8:209–216; Lorz et al., (1985) *Mol. Gen. Genet.* 199:178; Potrykus (1985) *Mol. Gen. Genet.* 199:183; Park et al., *J. Plant Biol.* (1995), 38(4), 365–71; Hiei et al., *Plant J.* (1994), 6:271–282]. The use of T-DNA to transform plant cells has received extensive study and is amply described [EP 120516; Hoekema, In: *The Binary Plant Vector System*, Offset-drukkerij Kanters B. V.; Alblasserdam (1985), Chapter V, Knauf, et al., *Genetic Analysis of Host Range Expression by Agrobacterium* In: *Molecular Genetics of the Bacteria-Plant Interaction*, Puhler, A. ed., Springer-Verlag, New York, 1983, p. 245; and An, et al., *EMBO J.* (1985) 4:277–284]. For introduction into plants, the chimeric genes of the invention can be inserted into binary vectors as described in the examples.

Other transformation methods are available to those skilled in the art, such as direct uptake of foreign DNA constructs [see EP 295959], techniques of electroporation [see Fromm et al. (1986) *Nature* (London) 319:791] or high-velocity ballistic bombardment with metal particles coated with the nucleic acid constructs [see Kline et al. (1987) *Nature* (London) 327:70, and see U.S. Pat. No. 4,945,050]. Once transformed, the cells can be regenerated by those skilled in the art. Of particular relevance are the recently described methods to transform foreign genes into commercially important crops, such as rapeseed [see De Block et al., (1989) *Plant Physiol.* 91:694–701], sunflower [Everett et al., (1987) *Bio/Technology* 5:1201], soybean [McCabe et al., (1988) *Bio/Technology* 6:923; Hinchee et al., (1988) *Bio/Technology* 6:915; Chee et al., (1989) *Plant Physiol.* 91:1212–1218; Christou et al., (1989) *Proc. Natl. Acad. Sci USA* 86:7500–7504; EP 301749], rice [Hiei et al., *Plant J.* (1994), 6:271–282], and corn [Gordon-Kamm et al., (1990) *Plant Cell* 2:603–618; Fromm et al., (1990) *Biotechnology* 8:833–839].

Transgenic plant cells are then placed in an appropriate selective medium for selection of transgenic cells which are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic such as kanamycin, G418, bleomycin, hygromycin, chloramphenicol, herbicide, or the like). The particular marker used will allow for selection of transformed cells as compared to cells lacking the DNA which has been introduced. Components of DNA constructs including transcription cassettes of this invention may be prepared from sequences which are native (endogenous) or foreign (exogenous) to the host. By "foreign" it is meant that the sequence is not found in the wild-type host into which the construct is introduced. Heterologous constructs will contain at least one region which is not native to the gene from which the transcription-initiation-region is derived. To confirm the presence of the transgenes in transgenic cells and plants, a Southern blot analysis can be performed using methods known to those skilled in the art.

CPL Translocation into the Chloroplast and Subsequent Processing

The present invention relies on the novel manipulation of a chloroplast targeting sequence to effect the translocation of the CPL gene product into chloroplasts with sufficient enzyme activity to yield commercially useful amounts of pHBA. Applicant has discovered that a key aspect of the invention is the inclusion of not only a transit peptide, but also a naturally occurring chloroplast cleavage site and a small portion of the transit peptide donor's mature N-terminus. The rational was to improve chloroplast uptake and processing of the foreign protein to obtain higher rates of conversion of chorismate to pHBA. However, following uptake into the organelle, the transit peptide is proteolytically removed by a chloroplast processing enzyme to yield a CPL variant that has a small polypeptide extension attached at its N-terminus. Unexpectedly, these additional amino acid resides do not interfere with CPL enzyme activity, and transformed plants expressing the instant chimeric protein accumulate significantly greater amounts of pHBA derivatives than have previously been reported. With regard to pHBA production, the need for this type of specificity has not been appreciated in the art.

The only reported instance of an attempt to express CPL in chloroplasts of living plants is recited in Siebert et al., *Plant Physiol.* 112:811–819 (1996). However, there are a number of important differences between the instant chimeric protein (e.g., TP-CPL) and the chloroplast-targeted version of *E. coli* CPL (e.g., TP-UbiC) recited in Siebert et al., Supra. For example, the instant chimera includes a chloroplast targeting sequence having a well-defined cleavage site for the efficient removal of the transit peptide. Additionally, removal of the transit peptide at this specific site results in the addition of 5 extra amino acids at the N-terminal region of the mature CPL polypeptide. In contrast, TP-UbiC recited in Siebert et al., Supra lacks a well-defined cleavage site and in addition contains a stretch of nine amino acids that are inserted between the putative transit peptide cleavage site and the initiator methionine residue of *E. coli* CPL. These differences are further elucidated in FIG. 1.

FIG. 1 shows an amino acid sequence alignment of the tomato Rubisco small subunit precursor complete with its transit peptide (line 1), TP-CPL (line 2), TP-UbiC (line 3), and *E. coli* CPL (line 1). The instant chimeric protein (line 2) consists of the chloroplast transit peptide of the tomato Rubisco small subunit precursor (green residues) plus the first four amino acid residues of "mature" Rubisco, fused to the initiator Met residue of *E. coli* CPL. Thus, TP-CPL contains not only the entire transit peptide, but also the highly conserved cleavage site where transit peptide removal would normally occur (e.g. between the Cys and Met residues as indicated by the arrow). Assuming that in the chloroplast TP-CPL is also cleaved at this position, the resulting protein would be a CPL variant with five additional amino acid residues at its N-terminus. Applicant has expressed the predicted chloroplast cleavage product of TP-CPL in E. coli, purified it to homogeneity, and shown it to be fully functional with regard to enzyme activity. Applicant has also demonstrated that proteolytic processing does occur at the Cys-Met junction, by purifying the "mature" polypeptide from transgenic tobacco plants that express the instant chimeric protein and subjecting its N-terminus to Edman degradation.

In contrast, as shown in line 3 of FIG. 1, TP-UbiC, (Siebert et al., Supra) does not contain the cleavage site where transit peptide removal would normally occur for the Rubisco small subunit precursor or any amino acid residues belonging to the mature Rubisco polypeptide (Mazur et al., Nuc Acids Res. 13:2373–2386 (1985); Berry-Lowe et al., J. Mol. and Appl. Gen. 1, 483–498 (1982)). Indeed, the Met residue that constitutes part of the scissile bond that is highly conserved in most plant species has been replaced with an Ala residue, which may or may not be recognized by the chloroplast processing enzyme. Additionally TP-UbiC, contains a stretch of nine additional amino acid residues (indicated in black letters) that are juxtapositioned between the Cys residue of the putative cleavage site and the initiator Met residue of E. coli CPL (FIG. 1). These extra amino acids were introduced as a cloning artifact in the construction of the TP-UbiC artificial fusion protein (Siebert et al, Supra), and their potential detrimental effect on chloroplast import and/or proteolytic processing was not explored. Regardless, even if cleavage of the transit peptide were to occur at the Cys-Ala junction as suggested, the resulting "mature" protein would contain nine extra amino acid residues at its N-terminus that could potentially have a detrimental effect on CPL enzyme activity (c.f. Table I, lines 2 and 4 of Siebert et al, Supra).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, DC (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. In any case where GCG program parameters were not prompted for, in these or any other GCG program, default values were used.

The meaning of abbreviations is as follows: "h" means hour(s), "min" means minute(s), "sec" means second(s), "d" means day(s), "mL" means milliliters, "L" means liters.

Example 1

PCR-Cloning of E. coli CPL

Two PCR primers were used to amplify the E. coli ubiC gene from genomic DNA, while adding unique restriction sites to its flanking regions for subsequent ligation into a high copy number plasmid. This gene codes for chorismate pyruvate lyase, which is referred to below as CPL. The primers used for this purpose were based on the published DNA sequences of the E. coli ubic gene (GenBank accession number M96268) and consisted of the following nucleotides:

Primer 1—(SEQ ID NO:1):
   5'-CTA CTC ATT Tca tat gTC ACA CCC CGC GTT AA-3'

Primer 2—(SEQ ID NO:2):
   5'-CAT CTT ACT aga tct TTA GTA CAA CGG TGA CGC C-3'

The underlined bases hybridize to the target gene, while lower case letters indicate the restriction sites (NdeI or BglII) that were added to the ends of the PCR primers.

Amplification of the E. coli ubic gene was achieved using Primers 1 and 2, and genomic DNA from E. coli strain W3110 (Campbell et al., Proc. Natl. Acad. Sci. 75:2276–2284 (1978)). Primer 1 hybridizes at the start of the gene and introduces a NdeI site at the protein's initiation codon, while Primer 2 hybridizes at the opposite end and provides a BglII site just past the termination codon. The 100-µl PCR reactions contained ~100 ng of genomic DNA and both primers at a final concentration of 0.5 µM. The other reaction components were provided by the GeneAmp PCR Reagent Kit (Perkin Elmer), according to the manufacturer's protocol. Amplification was carried out in a DNA Thermocycler 480 (Perkin Elmer) for 22 cycles, each comprising 1 min at 94° C., 1 min at 55° C., and 1 min at 72° C. Following the last cycle, there was a 7-min extension period at 72° C.

The PCR product was cut with NdeI and BglII, and the resulting fragment was ligated into the E. coli expression vector, pET-24a (+) (Novagen) that had been digested with NdeI and BamHI. The ligation reaction mixture was used to transform E. coli DH10B electocompetent cells (GibcoBRL) using a BTX Transfector 100 (Biotechnologies and Experimental Research Inc.) according to the manufacturer's protocol; growth was selected on LB media that contained kanamycin (50 µg/ml). Transformants that contained plasmids with a CPL insert were identified through PCR reactions, using primers 1 and 2 and individual resuspended colonies as the source of template; from hereon, this technique is simply referred to as "colony PCR". Plasmid DNA was isolated from a representative colony that yielded a PCR product of the correct size, and the entire insert corresponding to the CPL was sequenced completely to check for PCR errors; none were found. The plasmid that was selected for further manipulation is referred to below as "pET24a-CPL". The nucleotide sequence of the ORF for CPL in the pET24a E. coli expression construct and its predicted primary amino acid sequence are set forth in SEQ ID NO:3 and SEQ ID NO:4, respectively. Note that the coding region is identical to the ORF that is given in GenBank accession number M96268.

Example 2

Overexpression, Purification, and Characterization of Recombinant E. coli CPL

To generate sufficient quantities of CPL for enzyme characterization and antibody production, pET24a-CPL was introduced into E. coli BL21(DE3). This was done by electroporation using a BTX Transfector 100 (Biotechnologies and Experimental Research Inc.) according to the manufacturer's protocol. Growth was selected on LB media that contained kanamycin (50 µg/ml) and a single colony was selected for further manipulation. For production of recombinant protein, the plasmid-bearing strain was grown in liquid culture at 30° C. in the media described above, and the cells were induced with 0.15 mM IPTG at an $A_{600}$ nm of ~0.8. Following a 4.5-hr induction period under the same growth conditions, the cells were harvested by centrifugation and stored at −80° C. for subsequent use. Subsequent steps were at 0–4° C.

Frozen cell pellets were resuspended in ~3 volumes of 0.1 M Tris-HCl (pH 7.7), 5 mM $MgSO_4$, 1 mM dithiothreitol, 0.03 mg/ml Dnase I, 0.5 mM phenylmethanesulfonyl fluoride, and passed twice through a French pressure cell at 20,000 psi. Debris was removed by centrifugation (43, 0000× g, 1 h), and the cell-free extract, containing ~30 mg of protein/mL, was supplemented with glycerol (5%) and stored at −80° C. for subsequent use. Protein concentration was determined by the method of Lowry et al. (Lowry et al., J. Biol Chem. 193:265–275 (1951)), using BSA as a standard. SDS-PAGE analysis of the cell-free extract revealed that the recombinant protein was well expressed in E. coli BL21(DE3) under the growth conditions described, at levels exceeding 15% of the total soluble protein. However, only about 25% of the recombinant protein was recovered in the soluble fraction of the French press extract and this material was used for purification as described below.

The first step in the purification entailed anion exchange chromatography. An aliquot (1.0 mL) of the E. coli cell-free extract containing recombinant CPL was rapidly thawed to room temperature, diluted 1:1 with deionized water, and filtered through a 0.2 µm Acrodisc filter (Gelman Sciences, Cat. No. 4192). The entire sample was applied to a Mono Q HR 5/5 column (Pharmacia Biotech Inc), that was developed at 25° C. with Buffer Q (50 mM Tris-HCl, pH 7.7, 10 mM sodium sulfite, 1 mM EDTA) at a flow rate of 1 ml/min. Under these conditions, recombinant CPL does not adsorb to the anion exchange resin and elutes from the column isocratically during the first few minutes of the run. The column flow-through was collected in a single tube, supplemented with 5% (w/v) glycerol, and concentrated to a final volume of 450 µL in a Centricon-10 (Amicon Inc.) at 4° C. Following this simple procedure, the recombinant protein was ~90% pure as judged by SDS-PAGE (Laemmli U., Nature 227:680–685 (1970)) and Coomassie Blue staining. In the next step, 200 µL of the concentrated sample was applied to a 7.5×600 mm TSK G3000SW gel filtration column (TOSOH Corp.) that was preequilibrated with Buffer Q containing 0.3 M NaCl. The column was developed at a flow rate of 1.0 mL/min (25° C.), and highly purified recombinant CPL eluted between 19.7–21 min. The latter was kept on ice while the remaining half of the sample was processed in an identical manner. The peak fractions from the two gel filtration columns were pooled, supplemented with glycerol (5%), concentrated to ~12 mg of protein/mL, and stored at −80° C. for subsequent use. The yield of purified protein was ~3.7 mg, corresponding to about 12% of the total protein present in the cell-free extract. Visual inspection of overloaded Coomassie-stained gels indicated the final preparation of recombinant protein was >98% pure.

Purified recombinant CPL was subjected to Edman degradation, which revealed that the protein's initiator Met residue is removed in E. coli. Apart from this minor post-translational modification, however, the first 13 amino acids of recombinant CPL were identical to residues 2–14 of the protein that is shown in SEQ ID NO:4 (e.g., ORF of the authentic E. coil protein). The protomer molecular mass of purified recombinant CPL was 18644.6 daltons as determined by electrospray ionization mass spectrometry. This value is in excellent agreement with the molecular mass that is predicted from the DNA sequence (18645.49 daltons) if the initiator Met residue is not included. Based on these observations, it is reasonable to conclude that the initiator Met residue is also cleaved off of the native E. coli protein, since the nucleotide sequence of the latter is identical to recombinant CPL.

A continuous spectrophotometric assay was developed to assess the catalytic activity of the purified recombinant protein. The assay is based on the increase in absorbance at 246 nm that accompanies the conversion of chorismate to pHBA as result of the formation of the aromatic ring of the latter. Initial rates of product formation were measured at 25° C. in a quartz cuvette that contained 90 mM Tris-HCl (pH 7.6), 0.2 M NaCl, 100 µM barium chorismate (Sigma), and various amounts of purified recombinant CPL; reactions were initiated with enzyme. Product formation was calculated from the change in absorbance using an extinction coefficient of 11,220 M-1 for pHBA at 246 nm. The latter was determined under identical conditions at concentrations of pHBA ranging from 5 µM–100 µM; the absorbance of light was directly proportional to pHBA concentration. Based on the above assay, the turnover number for purified recombinant CPL at 25° C. was ~36 $min^{-1}$. Two other preparations of the same recombinant protein, purified on a much larger scale, yielded slightly higher turnover numbers under the same conditions (e.g., 41 $min^{-1}$ and 42 $min^{-1}$). The only value that is available in the literature for this enzyme is 49 $min^{-1}$ (Nichols et al., J. Bacteriol. 174:5309–5316 (1992)), but the assay was conducted at 37° C. Assuming that the CPL enzyme reaction is characterized by a Q10 (temperature coefficient) of at least 2, these observations indicate that the purified recombinant protein described above is fully active.

Example 3

Construction of a Chloroplast-targeted Version of CPL: TP-CPL

Chorismate, the physiological substrate of CPL, is an important branchpoint intermediate for the synthesis of numerous aromatic compounds, including the amino acids phenylalanine and tyrosine. In plants, chorismate is formed in the shikimate pathway which is localized in chloroplasts and other types of plastids (Siebert et al., *Plant Physiol.* 112:811–819 (1996)). It was therefore essential to provide CPL with an N-terminal chloroplast targeting sequence that would efficiently direct the foreign protein to chloroplasts, the site of chorismate production. This was accomplished by constructing a chimeric protein that consists of a chloroplast targeting sequence that is derived from the tomato Rubisco small subunit precursor protein fused to the initiator Met residue of CPL; the resulting fusion protein is referred to below as "TP-CPL". To generate a DNA fragment corresponding to the transit peptide of the Rubisco small subunit and first four amino acid residues of "mature" Rubisco, PCR was employed. The target for amplification was the plasmid pTSS1-91-(#2)-IBI (Siebert et al., *Plant Physiol.* 112:811–819 (1996)), which contains a full-length cDNA clone of the tomato Rubisco small subunit precursor for rbcS2 (Sugita et al., *Mol Gen Genet.* 209:247–256 (1987); Siebert et al., *Plant Physiol.* 112:811–819 (1996)). The following primers were used this reaction:
Primer 3
5'-CTA CTC ACT TAG ATC Tcc atg gCT TCC TCT GTC ATT TCT-3' (SEQ ID NO:5)
Primer 4
5'-CAT CTT ACT cat atg CCA CAC CTG CAT GCA GC-3' (SEQ ID NO:6)

The underlined portion of Primer 3 hybridizes to the first 21 nucleotides of the Rubisco small subunit precursor and introduces an NcoI site (lower case letters) at the initiator Met residue at the start of the chloroplast targeting sequence. As indicated, this primer also contains a BglII site (bold letters) at its 5' end, that is just upstream from the NcoI site. Primer 4 hybridizes at the other end of the chloroplast targeting sequence to nucleotides 167–184 of the ORF of the Rubisco small subunit precursor. A unique NdeI site was engineered into this primer (lower case letters) to allow attachment of the PCR fragment containing the chloroplast targeting sequence to the NdeI site that is situated at the start codon of CPL in the pET-24a expression construct. The 100-μl PCR reaction contained ~75 ng of pTSS1-91-(#2)-IBI and Primers 3 and 4 both at a final concentration of ~0.9 μM. Amplification was carried out in a DNA Thermocycler 480 (Perkin Elmer) for 25 cycles, each comprising 1 min at 94° C., 1 min at 55° C., and 1 min at 72° C.; the last cycle was followed by a 7-min extension period at 72° C. The PCR product was digested with BglII and NdeI, and ligated into pET24a-CPL that had been cleaved with the same restriction enzymes to remove a small DNA fragment (106 bp) that contained only vector sequence, including the T7 promoter. The ligation reaction mixture was introduced into *E. coli* DH10B using electroporation, and growth was selected on LB media with kanamycin (50 μg/ml). Transformants harboring plasmids with the inserted chloroplast targeting sequence were identified by colony PCR using Primers 2 and 3. A representative plasmid yielding a PCR product of the correct size was selected for further manipulation; this plasmid is referred to below as "pET24a-TP-CPL". To confirm the absence of PCR errors, the region of the plasmid corresponding to the amplified chloroplast targeting sequence was sequenced completely using custom designed primers. The nucleotide sequence of the ORF for TP-CPL and its predicted primary amino acid sequence are set forth in SEQ ID NO:7 and SEQ ID NO:8, respectively.

Example 4

The Predicted Chloroplast Cleavage Product of TP-CPL is Fully Active

A DNA fragment corresponding to the amino acid sequence of the predicted chloroplast cleavage product of TP-CPL (e.g., MQVWH-CPL) was generated by PCR using the insert in plasmid pet24a-TP-CPL as a template. The following primers were used for this reaction:
Primer 5
5'-CTA CTC ATT Tga aga cTG CAT GCA GGT GTG GCA T-3' (SEQ ID NO:9):
Primer 6
5'-CAT CTT ACT gtc gac TTT AGT ACA ACG GTG ACG C-3' (SEQ ID NO:10)

The underlined portion of Primer 5 binds at the 5' end of the TP-CPL gene insert and introduces a unique BBSI site (lower case letters) just upstream from the starting Met residue of the predicted chloroplast cleavage product (henceforth referred to as "ΔTP-CPL"). Primer 6 hybridizes at the opposite end of the gene insert and provides a unique SalI site (lower case letters) just past the termination codon. The PCR product was cut with BBSI (which leaves an NcoI-compatible "sticky end") and SalI, and the resulting fragment was ligated into the *E. coli* expression vector, pET-24d (+) (Novagen) that was digested with NcoI and SalI. The ligation reaction mixture was used to transform *E. coli* DH10B electro-competent cells (GibcoBRL) using a BTX Transfector 100 (Biotechnologies and Experimental Research Inc.) according to the manufacturer's protocol; growth was selected on LB media that contained kanamycin (50 μg/ml). Transformants that contained plasmids with a ΔTP-CPL insert were identified by colony PCR, using appropriate primers. A representative plasmid (e.g., pET24a-ΔTP-CPL) was isolated from a colony that yielded a PCR product of the correct size, and the insert corresponding to the ΔTP-CPL was completely sequenced to confirm the absence of PCR errors.

To express the recombinant protein for purification and kinetic analysis, pET24a-ΔTP-CPL was introduced into *E. coli* BL21 (DE3) using electroporation. The transformed cells were plated on LB media with kanamycin (50 μg/ml), and a representative colony was selected for further manipulation. A 300-ml culture was grown at 30° C. in the media described above, and IPTG was added to a final concentration of 0.15 mM at an $A_{600}$ nm of 0.8. Following a 4.5-hr induction period under the same conditions, the cells were harvested by centrifugation and stored at −80° C. Subsequent steps were at 0–4° C., unless otherwise specified.

The frozen cell pellet was resuspended in 2.5 ml of a solution containing 0.1 M Tris-HCl (pH 7.7), 5 mM $MgSO_4$, 1 mM dithiothreitol, 0.03 mg/ml Dnase I, 0.5 mM phenylmethanesulfonyl fluoride, and passed twice through a French pressure cell at 20,000 psi. The cell-free extract was subjected to centrifugation (43,000× g, 25 min), and the supernatant (4.5 ml) was carefully removed, supplemented with 5% glycerol and stored at −80° C. for subsequent use. The purification protocol for ΔTP-CPL was essentially identical to that described for unmodified, recombinant *E. coli* CPL. Briefly, the entire sample above was thawed and concentrated to a final volume of 2.5 ml using a Centriprep-10 (Amicon Inc). The sample was then exchanged into Buffer Q using a PD-10 gel filtration column (Pharmacia Biotech Inc) that was preequilibrated with Buffer Q, according to the manufacturer's protocol. The volume was reduced to 2 ml in a Centriprep-10, and the entire sample was loaded onto a Mono Q HR 10/10 column (Pharmacia Biotech Inc), that was developed at 4 ml/min (25° C.) with Buffer Q. The material eluting between 2–3 minutes was collected, and glycerol was added to a final concentration of 5% (v/v). The sample was concentrated to 200 μl in a Centricon-10 (Amicon Inc), and applied to a 7.5×600 mm TSK G3000SW gel filtration column (TOSOH Corp.). The column was developed at 1 ml/min with Buffer Q containing 0.3 M NaCl (25° C.), and recombinant ΔTP-CPL eluted between 20.7–22 min. The fraction containing the purified recombinant protein was supplemented with 5% glycerol, concentrated to ~0.7 mg of protein per ml, and stored at −80° C. for subsequent use.

The enzymatic activity of purified, recombinant ΔTP-CPL was determined at 25° C., using the spectrophotometric assay that was described in Example 2. Under these conditions, the turnover number was 40.7 min−1. This value is virtually identical to that obtained with purified, recombinant, *E. coli* CPL without an N-terminal extension (e.g. 36–42 min$^{-1}$). This observation clearly demonstrates that the 5 extra amino acid residues that are fused to the N-terminus of ΔTP-CPL do not compromise enzyme activity, and further suggests that the predicted chloroplast cleavage product of TP-CPL is probably fully active.

Example 5

In Vitro Protein Import: TP-CPL is Imported into Isolated Chloroplasts

Before introducing TP-CPL into higher plants it was important to show that it could be taken up by chloroplasts. This was done by synthesizing a radioactive version of the artificial fusion protein and subjecting it to classical chloroplast protein import experiments. The first step was to generate a DNA construct that could be used to radiolabel the protein with [$^{35}$S]methionine for transport experiments. To do this, the sequence encoding TP-CPL was modified for insertion into the MscI and BglII sites of the in vitro transcription/translation vector, pCITE4a(+) (Novagen) using Primers 7 and 8, and the insert in plasmid pet24A-TP-CPL as a template for PCR-amplification.

Primer 7
5'-CTA CTC ATT tgg cca GCT CTG TCA TTT CTT CAG CAG C-3' (SEQ ID NO:11)
Primer 8
5'-CAT CTT ACT aga tct TTA GTA CAA CGG TGA C-3' (SEQ ID NO:12)

Primer 7 hybridizes to a stretch of nucleotides just past the start codon of TP-CPL (underlined region), and incorporates a unique MscI site (indicated by lower case letters) at the initiator Met residue. Primer 8 binds at the other end of the gene insert and introduces a unique BglII site immediately after the stop codon. Neither primer introduces any amino acid changes in the artificial fusion protein. The resulting PCR fragment was digested with MscI and BglII, and ligated into pCITE4a(+) that was cut with MscI and BamHI; BglII and BamHi generate compatible "sticky ends". The ligation reaction mixture was introduced into *E. coli* DH10B using electroporation, and the transformed cells were plated on LB media that contained ampicillin (100 μg/ml). A representative colony harboring a plasmid with the correct insert (identified by colony PCR, using appropriate primers) was selected for further manipulation. The plasmid DNA was sequenced completely to confirm the absence of PCR errors.

Next, the plasmid construct described above was subjected to in vitro transcription/translation using [$^{35}$S] methionine and the "Single Tube Protein System 2, T7" kit (Novagen), according to the vendor's protocol. Reactions were terminated with 2× import buffer containing 60 mM unlabeled methionine (Viitanen et al., *J. Biol. Chem.* 263:15000–15007 (1988)). Chloroplast were isolated from 14-day-old pea seedlings (*Pisum sativum*) and subjected to in vitro import assays (Viitanen et al., *J. Biol. Chem.* 263:15000–15007 (1988)) using radiolabeled TP-CPL. Protease post-treatment was used to distinguish between bound and imported polypeptides (Cline et al., *J. Biol. Chem.* 260:3691–3696 (1985)). Intact plastids were then repurified by centrifugation through Percoll cushions, resuspended in 150 μl of 2× gel sample buffer, and analyzed by SDS-PAGE/ fluorography as previously described (Viitanen et al., *J. Biol. Chem.* 263:15000–15007 (1988)).

In vitro transcription/translation of TP-CPL resulted in the synthesis of a radioactive polypeptide with an apparent molecular mass of ~25 kDa (based on migration during SDS-PAGE (Laemmli, U. K., Nature 227:680–685 (1970)), consistent with the value predicted from its DNA sequence (25188 Da). In the presence of ATP, this polypeptide was taken up by chloroplasts and processed to a smaller size, which appeared to co-migrate with Coomassie-stained purified, recombinant ΔTP-CPL (e.g. the predicted chloroplast cleavage product of TP-CPL). Classical protease protection experiments established that the radioactive polypeptide that was recovered with intact chloroplasts following import assays had actually been internalized.

In contrast, when chloroplasts were incubated under conditions that do support protein import (e.g., in the dark, without ATP), uptake and processing of TP-CPL were not observed. Under non-energized conditions, the only radioactive band recovered with intact plastids was the full-length fusion protein, TP-CPL. Moreover, the radioactive band corresponding to the latter completely disappeared after treatment with protease, demonstrating that it had not been imported but was merely bound to the outer chloroplast membrane. Taken together, these results clearly demonstrate that the chloroplast targeting sequence that is attached to the N-terminus of TP-CPL, is able to direct the artificial fusion protein to chloroplasts, and after uptake into the organelle, proteolytic processing occurs in the expected manner.

Example 6

Construction of the Expression Plasmid Used for Tobacco and Arabidopsis Transformation Having established that TP-CPL is efficiently taken up by chloroplasts (Example 5) and cleaved to a novel protein with high CPL activity (Example 4) it was decided to introduce it into plants. To generate a construct that could be used for constitutive expression in tobacco and arabidopsis, the DNA fragment corresponding to the full-length TP-CPL fusion protein was subcloned into a modified version of plasmid pML63. The latter was derived from pML40, which contains the following genetic elements: a CaMV 35S promoter, a cab leader sequence, the uidA coding region, and the NOS polyadenylation signal sequence. Briefly, the CaMV 35S promoter is a 1.3 kb DNA fragment that extends 8 base pairs past the transcription start site (Odell et al., (1985) *Nature* 303:810–812). Operably linked to its 3' end is the cab leader sequence, a 60 bp untranslated double-stranded piece of DNA that was obtained from the chlorophyll a/b binding protein gene 22L (Harpster et al. (1988) *Mol. Gen. Genet.* 212:182–190). Fused to the 3' end of the cab leader is the uidA gene (Jefferson et al. (1987) *EMBO J.* 6:3901) that encodes the protein β-glucuronidase (e.g., "GUS"). Finally, attached to 3' end of the GUS gene is an 800 bp DNA fragment containing the polyadenylation signal sequence from the nopaline synthase (e.g. "NOS") gene (Depicker et al. (1982) *J. Mol. Appl. Genet.* 1:561–564). These DNA fragments, together comprising a 35S-GUS chimeric gene, were inserted by standard cloning techniques into the vector pGEM9Zf (−) (Promega; Madison Wis.) to yield plasmid pMH40.

Plasmid pML63, which is basically the same as pMH40 but has a truncated version of the 3' NOS terminator sequence, was generated in the following manner. First, pMH40 was digested with Sal I and the two resulting DNA fragments of 4.03 kb and 2.9 kb were re-ligated to yield a plasmid with the 35S promoter/cab22 leader/GUS gene/3' NOS terminator cassette in the opposite orientation. The resulting construct was then digested with Asp718 I and Hind III to release a 770 bp fragment that contained the 3' NOS terminator sequence. The latter was discarded and replaced with a shorter version that was generated by PCR using pMH40 as a template and Primers 9 and 10.

Primer 9:
5'-CCC GGG GGT ACC TAA AGA AGG AGT GCG TCG AAG-3' (SEQ ID NO:13):

Primer 10:
5'-GAT ATC AAG CTT TCT AGA GTC GAC ATC GAT CTA GTA ACA TAG ATG A 3' (SEQ ID NO: 14):

The PCR product was digested with Hind III and Asp718 I to yield a 298 bp fragment that contains 279 bp of the 3' NOS terminator sequence, starting at nucleotide 1277 (the TAA stop codon) and ending at nucleotide 1556 of the published sequence (Depicker et al., *J. Mol Appl Genet* (1982) 1:561–574). Ligation of this PCR fragment into pML3 yielded the plasmid pML63.

Figure 2:
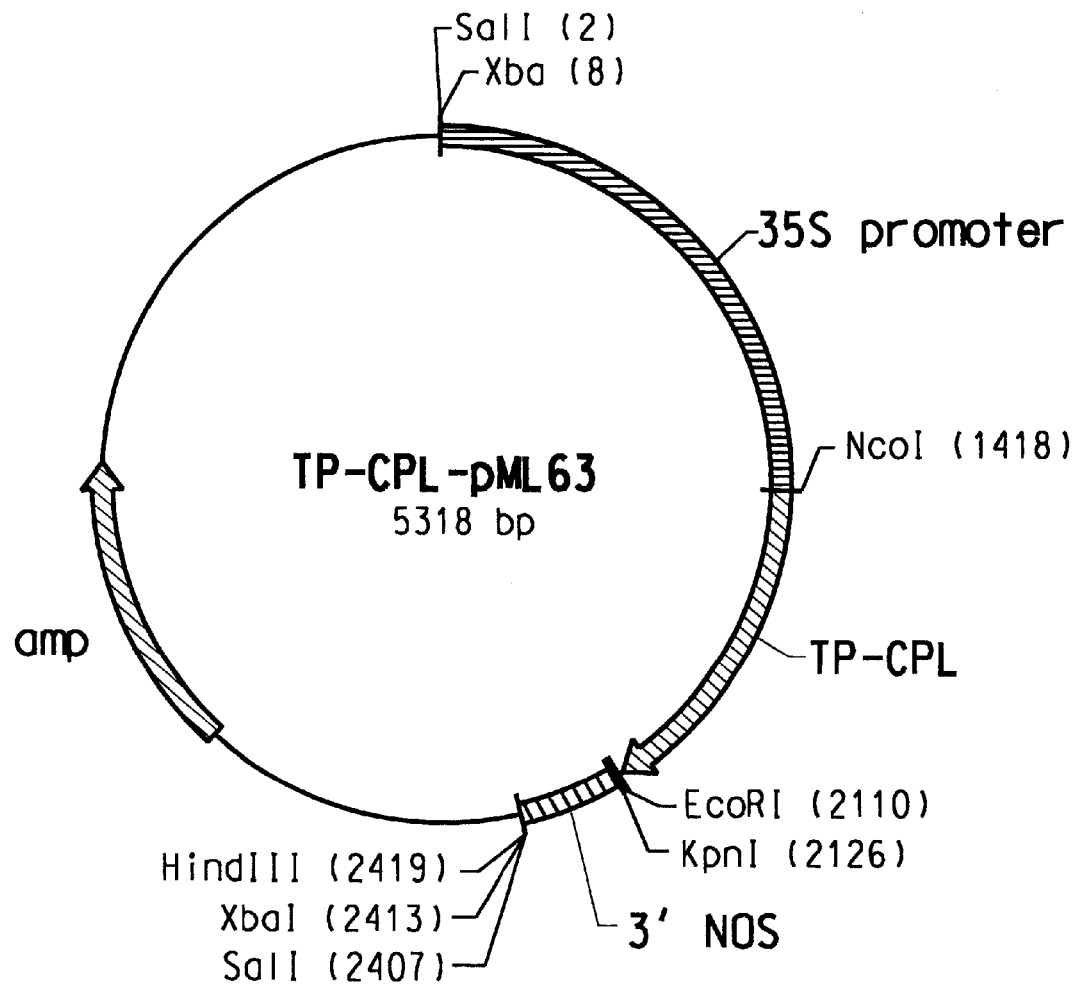
FIG. 2 shows a schematic representation (circle diagram) of the intermediate plasmid, "TP-CPL-pML63", and relevant restriction sites.

As indicated above, pML63 contains the GUS coding region under the control of the 35S promoter and a truncated version of the 3' NOS terminator. It therefore contains all of the transcriptional information that is necessary for the constitutive expression of GUS in plants. To generate an analogous construct for TP-CPL, plasmid pML63 was digested with Nco I and EcoRI. This manipulation releases only the GUS gene insert, leaving the regulatory flanking sequences and the rest of the vector intact. Plasmid pet24a-TP-CPL was also treated with NcoI and EcoRI, which liberates the entire coding region of the TP-CPL fusion protein. The small DNA fragment (693 bp) corresponding to the latter was purified by agarose gel electrophoresis and subjected to a standard ligation reaction with the large vector fragment (4.63 bp) that was obtained from cutting pML63 with Nco I and Eco RI. The ligation reaction mixture was introduced into *E. coli* DH10B using electroporation, and growth was selected on LB media that contained ampicillin (100 μg/ml). Transformants harboring plasmids with the inserted TP-CPL coding sequence were identified by colony PCR using Primers 2 and 3. A representative plasmid that yielded a PCR product of the correct size was selected for further manipulation. A schematic representation of the final construct, referred to below as "TP-CPL-pML63", is shown in FIG. 2.

Figure 3:
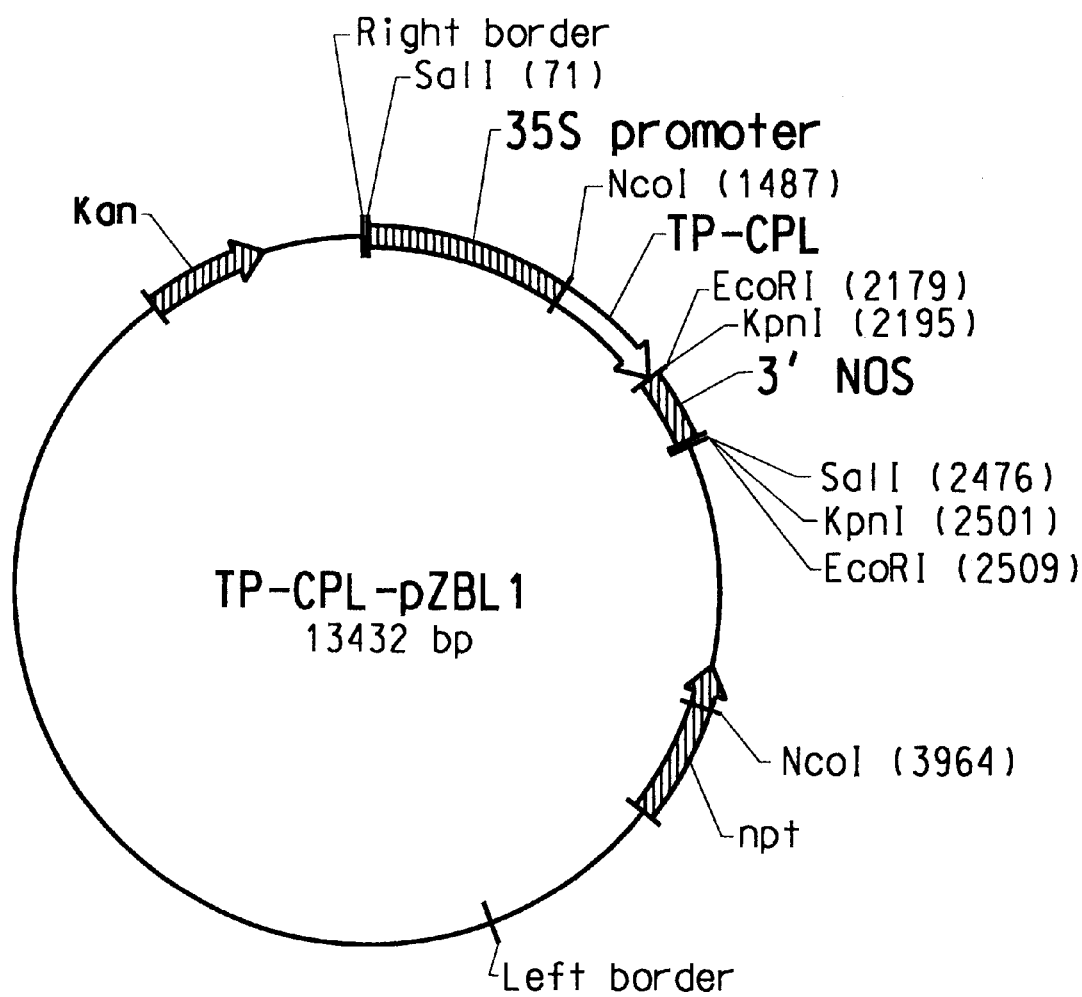
FIG. 3 shows a schematic representation (circle diagram) of the binary vector plant expression construct, "TP-CPL-pZBL1", that was used for transformation of tobacco and arabidopsis after introduction into Agrobacterium.

The binary vector that was used for Agrobacterium-mediated, leaf disc transformation of tobacco was the plasmid pZBL1 which was deposited with the ATCC on June 24, 1997 and bears the accession number 209128. PZBL1 contains the origin of replication from pBR322, the bacterial nptI kanamycin resistance gene, the replication and stability regions of the *Pseudomonas aeruginosa* plasmid pVS1 (Itoh et al, 1984), T-DNA borders described by van den Elzen et al., 1985 wherein the OCS enhancer (extending from −320 to −116 of the OCS promoter (Greve et al., 1983, *J. Mol. Appl. Genet.* 1:499–511)) that is part of the right border fragment is removed, and a NOS/P-nptII-OCS 3' gene to serve as a kanamycin resistant plant selection marker. For expression of TP-CPL, plasmid pZBL 1 was digested with Sal I which cuts at a unique site between the right and left borders that is ideally situated for the insertion of foreign genes and stable integration into the plant genome. To minimize the possibility of re-ligation without an insert, the cut vector was dephosphorylated using Calf Intestinal Alkaline Phosphatase (GibcoBRL) according by the manufacturer's recommendations. To obtain the fragment that would be inserted into the binary vector, plasmid TP-CPL-pML63 was also digested with Sal I. This treatment releases the entire transcriptional unit for the TP-CPL fusion gene (e.g., 35S promoter/cab22 leader/TP-CPL/3' NOS terminator) as a 2.4 kb DNA fragment. The latter was purified by agarose gel electrophoresis and subjected to a standard ligation reaction with the dephosphorylated 11.0 kb fragment that was obtained from pZBL1 as described above. The ligation reaction mixture was introduced into *E. coli* DH10B using electroporation, and growth was selected on LB media with kanamycin (50 μg/ml). Transformants harboring plasmids with the TP-CPL fusion gene were identified by colony PCR using Primers 2 and 3, and the orientation of the insert was determined by restriction digestion analysis using Kpn I. In the plasmid that was selected for further manipulation, referred to below as "TP-CPL-pZBL1", the start codon for TP-CPL is adjacent to the right border fragment of the T-DNA as shown schematically in FIG. 3. As described below, this expression construct was used for the transformation of tobacco and arabidopsis for overproduction of pHBA.

Example 7

Generation of Transgenic Tobacco Plants

Plasmid TP-CPL-pZBL 1 was introduced into *Agrobacterium tumefaciens* strain LBA4404 (Hoekema et al., *Nature* 303:179–180 (1983) using the freeze-thaw transformation procedure (Holsters et al, *Mol. Gen. Genet.* 163:181–187). The cells were plated at 28° C. on YEP media (10 g Tryptone, 10 g Yeast Extract, and 5 g NaCl per liter) that also contained kanamycin (1000 μg/ml) and rifampicin (20 μg/ml). Colonies harboring the binary construct were identified by PCR using appropriate primers.

Potted tobacco plants (*Nicotiana tabacum* cv. Xanthi) for leaf disk infections were grown in a growth chamber maintained for a 14 hr, 21° C. day, 10 hr, 18° C. night cycle, with approximately 80% relative humidity, under mixed cool white fluorescent and incandescent lights. Agrobacterium-mediated, leaf disk transformations were performed essentially as described by De Blaere et al., *Meth. Enzymol.* 153:277–292) with the following modifications. Leaf disks, 8 mm in diameter, were prepared from whole leaves using a sterile paper punch and plants that were 4–6 weeks old. Leaf disks were inoculated by submerging them for 30 mins in concentrated solution of Agrobacterium harboring TP-CPL-pZBL1 resuspended to an OD600 of ~Z in Murashige Minamal Organics media. Inoculated leaf disks were placed directly on media, that contained (per liter) 30 g of sucrose, 1 mg of 6-benzylaminopurine (BAP), 0.1 mg of napthaleneacetic acid, 8 g of agar, and 1 package of Murashige's Minimal Organics Medium that was obtained from GibcoBRL (cat. #23118-029). After incubation for 3 days at 28° C. in the light, leaf disks were transferred to fresh media of the same composition that also contained kanamycin (300 μg/ml) and cefotaxime (500 μg/ml) to select for the growth of transformed tobacco cells and eliminate residual Agrobacterium. Leaf disks were incubated under the growth conditions described above for 3 weeks and were then transferred at 3-week intervals to fresh media of the same composition until optimal shoot size was obtained for root induction. Shoots were rooted on media containing (per liter) 1 package of Murashige's Minimal Organics Medium,

Example 8

Chemical Synthesis of pHBA Glucoside Standards

To synthesize the pHBA ester glucoside, 110 mmol of 4-hydroxybenzoic acid was combined with 55 mmol bis (tributyltin)oxide in 1 L benzene. The mixture was heated to reflux for 16 h under an atmosphere of nitrogen with an azeotrope apparatus in place. The benzene was removed under reduced pressure to yield a clear oil which is predominantly the 4-hydroxybenzoic tributyltin ester (Ogawa et al., (1982) Tetrahedron 36:2641–2648). Next, 25 mmol of acetobromo-a-D-glucose in 1.2 L of 1,2-dichloroethane was added to 25 mmol of the 4-hydroxybenzoic tributyltin ester intermediate, and this was followed by the addition of 12.5 mmol of tetrabutylammonium bromide. The mixture was heated to reflux under a nitrogen atmosphere for 3 h, and progress of the reaction was monitored by TLC with detection by charring with sulfuric acid. The solvent was removed under reduced pressure, and the acetyl protected pHBA ester glucoside was purified on silica gel, using a 1:1 mixture of ethyl acetate and hexane for elution. The acetyl protecting groups were then selectively saponified for 3 h with 1 equivalent of potassium carbonate in a 10% solution of methanol in water. The solvent was removed under reduced pressure and the pHBA ester glucoside was cleanly triturated with methanol. The latter was removed by filtration, and the resulting white powder exhibited a melting point of 209–210° C. The chemical structure of the pHBA ester glucoside was confirmed by $^1$H NMR.

For synthesis of the pHBA acyl glucoside, 16.4 mmol of methyl 4-hydroxybenzoate and 14.6 mmol of acetobromo-a-D-glucose were dissolved in 7.0 ml of anhydrous pyridine, and this was followed by the addition of 23.3 mmol of 99.99% silver oxide. The reaction was stirred, under a nitrogen atmosphere, for 3 h at room temperature. The insoluble silver salts were then collected by filtration, washed with pyridine, and the combined filtrate and washings were concentrated under reduced pressure and poured into a mixture of ice cold water. The dark brown solid was collected, rinsed with water, and dissolved in a 1:1 mixture of chloroform and methylene chloride which was subsequently dried using sodium carbonate as a drying agent. The solution was filtered through celite and the solvents were removed under reduced pressure. The hydroxy linked methyl benzoate, acetyl protected glycoside (Durkee et al., (1979) Carbohydrate Research 77:252–254) was then purified using silica gel chromatography; the 35 column was eluted with a 1:2 mixture of ethyl acetate and hexane. The purified compound was dissolved in 40 ml of methanol and 1.5 mmol of sodium methoxide was added. After 4.5 h, the solution had turned yellow and the solvent was removed under reduced pressure; the resulting residue was dissolved in 25 ml of water. The solution was concentrated to ~5 mls and allowed to crystallize to yield the hydroxy linked methylbenzoate glycoside; the crystals were collected and dried under high vacuum. To selectively saponify the methyl ester group, 2.5 mmol of the hydroxy linked methylbenzoate glycoside was dissolved in 25 ml water and 2.5 ml of 1 M NaOH was added. After stirring overnight at room temperature, the solution was neutralized, concentrated to ~5 ml, and allowed to crystallize to yield the desired pHBA acyl glucoside. The melting point of this compound was found to be 108–110° C., and its chemical structure was confirmed by $^1$H NMR.

Example 9

Preparation of Tobacco Leaf Samples for Analysis of pHBA Glucosides

Healthy leaves, measuring ~15 cm along the midvein, were selected for from the top third of the tobacco plant stem. The tissue (100 mg fresh weight) was rapidly removed with scissors from the distal ⅓ portion of the leaf and placed in a Biopulverizer H Tube (cat. no. 6570-201 or 6540-401) that contained a ceramic bead; both of the latter were obtained from BIO 101 (Joshua Way, Vista, Calif.). Following the addition of 1 ml of methanol, the tubes were capped and mechanically agitated for 40 s using a Savant FastPrep FP120 tissue disruption apparatus that was operating at a speed of 5 m/s. Next, the tubes were placed on a rotary shaker and vigorously agitated at 400 rpm for 1 h at room temperature. The extract was clarified by centrifugation (10,000× g, 10 mins) using a conventional tabletop microfuge, and the supernatant which contained both pHBA glucosides was carefully removed to an empty tube. The remaining insoluble leaf material was re-extracted with 0.5 ml of methanol for 30 min at room temperature using the rotary shaker and the conditions described above. The supernatant resulting from the second extraction was combined with the first, and the samples were stored at −20° C. for subsequent processing. The volume of methanol that was added to each sample of leaf material and the final volume that was recovered after extraction and centrifugation were determined gravimetrically using an analytical balance and the density of methanol to convert mass to volume.

Figure 4:
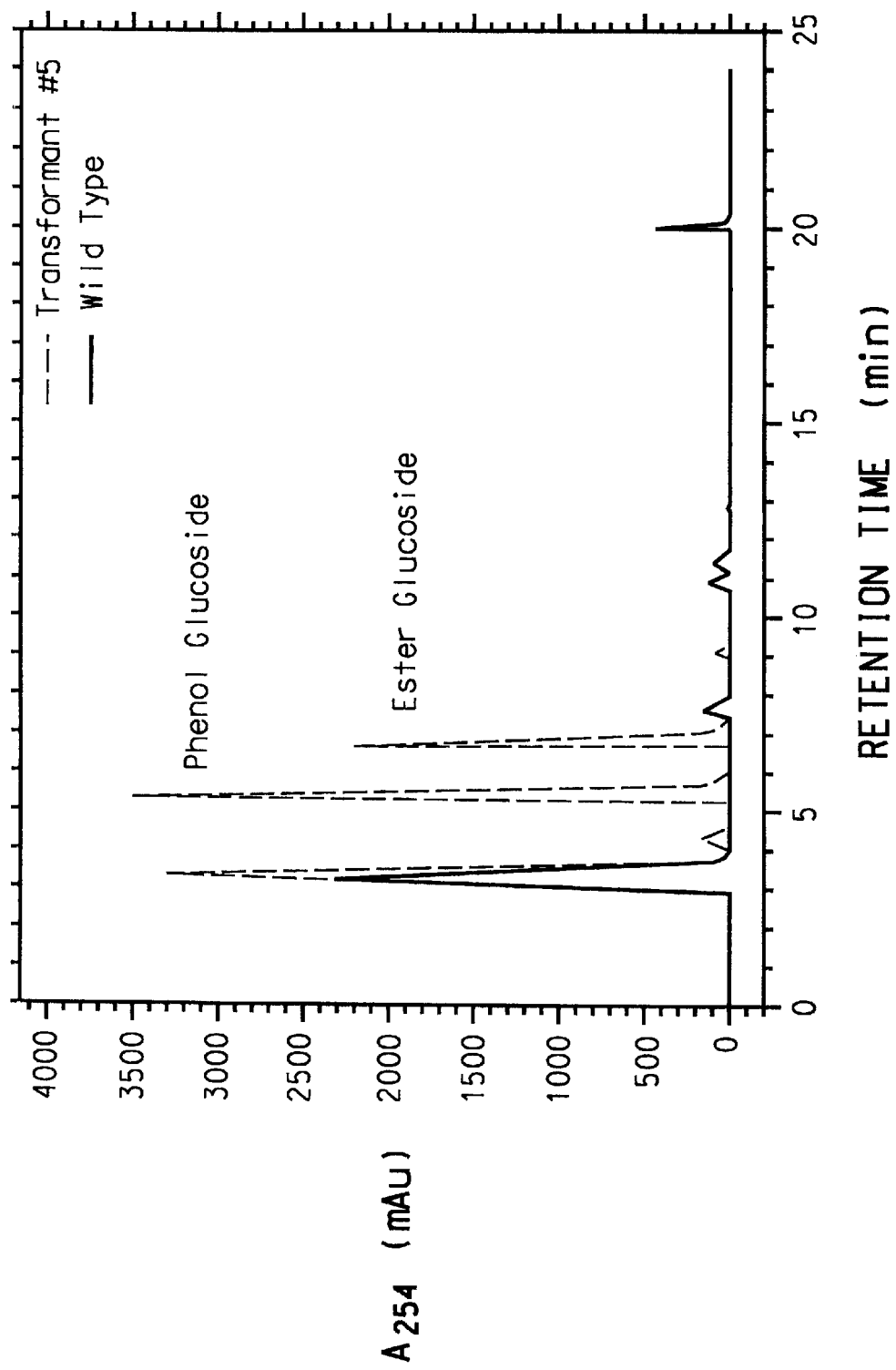
FIG. 4 shows a representative HPLC tracing of leaf tissue extract prepared from a transgenic tobacco plant expressing TP-CPL (Transformant #5) compared to a wildtype plant.

Further processing of the samples for HPLC analysis was as follows. Unless otherwise stated, all steps were conducted at room temperature. An aliquot of the methanol extract was transferred to a microfuge tube, and its exact volume was determined as described above. The solvent was removed under vacuum in a Speed-Vac (Savant Instruments) with the heat setting on and the sample was taken to complete dryness. The dry residue was dissolved in 100 μl of 0.2 N HCl and 0.7 mL water-saturated diethyl ether was added. After vigorous vortex mixing and centrifugation, the ether phase was carefully removed and discarded, and the sample was re-extracted with ether as described above. An aliquot of the remaining aqueous phase (50 μl) was then filtered through a 0.22 um cellulose acetate filter (Costar EZ-spin) and injected onto a Vydac 218TP54 PROTEIN AND PEPTIDE C18 column that was pre-equilibrated at 1 ml/min with 90% Buffer A (0.1% formic acid in water) and 10% Buffer B (methanol). Upon sample injection, the column was developed with a linear gradient that was generated over 20 min period to a final concentration of 50% Buffer B. The flow rate was 1 ml/min. Elution of the phenolic and ester pHBA glucosides was monitored spectrophotometrically at 254 nm. FIG. 4 shows representative HPLC tracings of a tobacco plant expressing TP-CPL (Transformant #5) and a wildtype plant.

Authentic pHBA glucoside standards (see above) were used to calibrate the HPLC runs for retention times, and extinction coefficients for both compounds were accurately determined under the HPLC conditions employed. Thus, peak areas were integrated using the software provided with the H/P Chemstation, and the values obtained with known amounts of the appropriate standards were used to quantitate micrograms of pHBA glucosides per injection. After accounting for dilution and the fraction of the original methanol extract that was injected on the column, the numbers were corrected to reflect total recovery from the leaf sample analyzed. This, coupled with an individual measurement of the dry weight of the plant tissue analyzed (e.g. obtained from the same plant, on the same day), enabled the expression of pHBA-glucosides as a percentage dry weight.

Example 10

Segregation of Kanamycin-resistance in the First Self-crossed Filial Generation

Seeds from primary tobacco Transformant #34 that resulted from self-crossing were surface sterilized by immersion in a 10% bleach solution [Clorox® containing 5.25% Na(OCl)$_2$] that also contained 0.1% SDS for 30 min at room temperature with gentle agitation. The germination frequency of 200 seeds without antibiotic selection was 97.5%. In contrast, of the 500 seeds that were plated on germination media that also contained kanamycin (300 μg/ml), approximately 20% displayed the recessive phenotype (e.g., the ratio of kanamycin sensitive seeds to kanamycin resistant seeds was 1:4). Since the segregation ratio for Transformant #34 is very close to the theoretical ratio of 1:3 for a monogenic dominant trait (e.g., as opposed to a 1:16 ratio that is characteristic of a double-loci event), it may be concluded that the selectable marker and TP-CPL gene expression construct were stably integrated into the genome at a single loci.

Example 11

Determination of CPL Enzyme Activity in Tobacco Leaf Extracts

Leaf tissue extracts from wildtype and transgenic tobacco plants were prepared and assayed for CPL enzyme activity as previously described (Siebert et al., *Plant Physiol.* 112:811–819 (1996)) with minor modifications. Leaf samples (2 g wet weight) were homogenized in an ice-cold mortar with 2.6 ml of a solution containing 50 mM Tris-HCl (pH 7.5), 0.1% β-mercaptoethanol, 1 mM EDTA, 1 mM phenylmethanesulfonyl fluoride, and 75 mg/ml polyvinylpoly-pyrrolidone. Unless otherwise indicated, all subsequent steps were conducted at 0–4° C. Following low-speed centrifugation to remove insoluble material, the sample was buffer exchanged into 50 mM Tris-HCl (pH 8.0), 10 mM EDTA, and 200 mM NaCl, using a PD-10 gel filtration column (Pharmacia Biotech Inc) according to the manufacturer's recommendations. Protein concentration was determined using the Bio-Rad (Bradford) protein assay.

CPL enzyme assays were conducted as follows. The basic reaction mixture (final volume, 500 μl) contained 50 mM Tris pH 8.0 (at 37° C.), 10 mM EDTA, 200 mM NaCl, and 150 μM of purified barium chorismate (Siebert et al. Microbiology 140:897–904 (1994)). Following a 5-min incubation period at 37° C., reactions were initiated with tobacco leaf extract that contained 50 μg of protein. Reactions were terminated after 2 min at 37° C. with 0.3 ml of 0.75 M sodium acetate (pH 4), and the amount of pHBA that was produced in the reaction was determined. To monitor the recovery of product, each tube received 9,500 dpm of [1$^4$C]-labeled pHBA (55 mCi/mmol) as an internal standard. The mixtures were extracted with 1 ml of H$_2$O-saturated ethyl acetate, and the organic phase was collected and taken to dryness. The amount of pHBA was then quantitatively determined by reverse phase HPLC, using the exact same column and conditions that were described in Example 9. The peak corresponding to pHBA was collected and the amount of radioactivity was determined by liquid scintillation counting. Values reported below for CPL enzyme activity are expressed as pkats per mg protein, and have been corrected for recovery of the internal standard and the small amount of pHBA that is generated from chorismate through spontaneous decomposition (Siebert et al., *Plant Physiol.* 112:811–819 (1996)).

Example 12

Analysis of Transgenic Tobacco Plants Expressing TP-CPL

Figure 5:
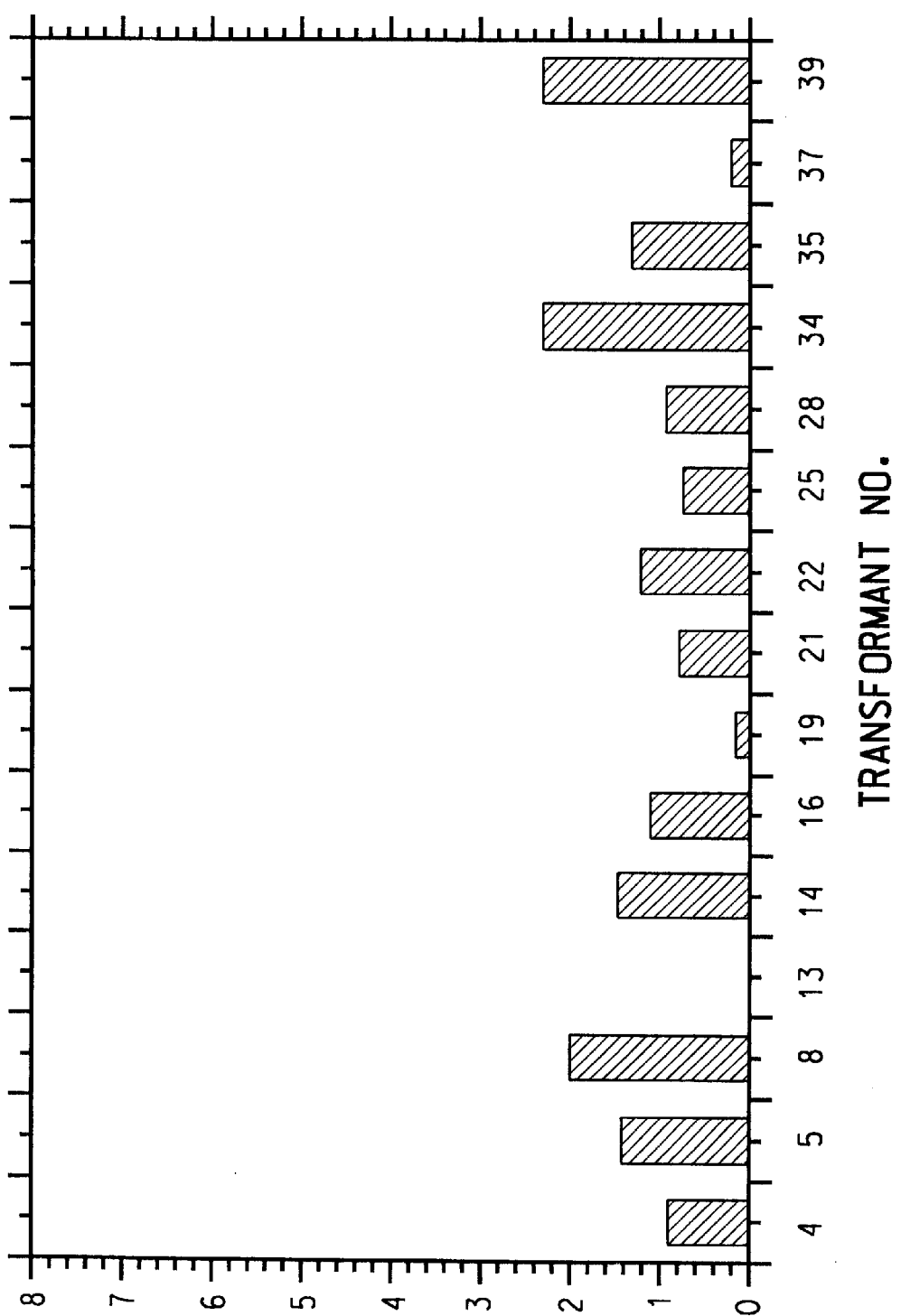
FIG. 5 shows the total pHBA-glucoside content of 15 different transgenic tobacco plants expressing TP-CPL. The analysis was conducted on fresh leaf material that was obtained 5 weeks after the primary transformants were transferred to soil.

As described above, TP-CPL was introduced into tobacco (*Nicotiana tabacum*) using agrobacterium-mediated, leaf disc transformation to determine its influence on the accumulation of pHBA glucosides. That this artificial fusion protein is indeed superior to other chloroplast-targeted versions of *E. coli* CPL that have previously been used to elevate pHBA levels in plants (Siebert et al., *Plant Physiol.* 112:811–819 (1996); Sommer et al., *Plant Cell Reports* 17:891–896 (1998)), is apparent from the data shown in FIG. 5. This analysis was conducted on leaf tissue that was obtained from 15 tobacco plants (primary transformants) that resulted from different transformation events. Note that the samples were taken only 5 weeks after the plants had been transferred to soil. As anticipated, the primary transformants exhibited various levels of pHBA glucosides, ranging from 0–2.3% of the total dry weight. This type of variation is typically observed in nearly all plant transformation experiments, and presumably reflects different levels of gene expression that result from so-called "positional" effects (e.g., stable integration of the trait gene at different locations in the genome) and transgene copy number. That a similar phenomena also occurred in the present study is supported by Western blot analysis of the tobacco transformants using antisera directed against purified recombinant *E. coli* CPL. For example, although the majority of the plants (e.g., 14/15) had immunologically detectable levels of the foreign protein, there was considerable variation in the levels of expression. Generally speaking, however, there was a positive correlation between the strength of the Western signal and the accumulation of pHBA glucosides, consistent with previous observations (Siebert et al., *Plant Physiol.* 112:811–819 (1996)); Sommer et al., *Plant Cell Physiol.* 39(11):1240–1244 (1998); Sommer et al., *Plant Cell Reports* 17:891–896 (1998)).

Based on dry weight, the average pHBA glucoside content of the 5-week-old tobacco plants was 1.12% (+/− 0.186%), where the number in parenthesis is the standard error of the mean. More important, in only three of the primary transformants (#13, #19, and #37) was the level of pHBA glucosides lower than 0.52%, which was the highest level that was obtained in a similar study with the TP-UbiC artificial fusion protein (Siebert et al., *Plant Physiol.* 112:811–819 (1996). Furthermore, the three best plants in the present study (#8, #34, and #39) had pHBA glucoside contents that were at least 2% of dry weight.

To examine the stability of the desired phenotype, three of the transgenic tobacco plants (#4, #5, and #34) were monitored over an extended period of time, up to the stage of seed formation. It was possible that the plants might not be able to maintain such high levels of pHBA glucosides as they continued to develop. However, as shown in FIG. 6, this was not the case. As the plants grew older, their leaf content of pHBA glucosides increased dramatically. For example, in Transformant #5, the total pHBA glucoside levels were 0.5%, 1.6%, 7.2%, and 10% of the total dry weight, when samples were analyzed 1, 5, 11, and 13 weeks after transferring the plant to soil. The 13-week value represents a nearly 20-fold increase over the results obtained with TP-UbiC, and corresponds to a pHBA content of 4.5% after correcting for the mass of the associated glucose molecule. Despite these very high levels of the secondary metabolite, the transgenic tobacco plants seemed perfectly normal and were morphologically indistinguishable from wildtype plants.

To follow the fate of the foreign gene and the associated phenotype of pHBA accumulation into the next generation, Transformant #34 was selected for further analysis. As a 13-week-old primary transformant, the pHBA glucoside content of this plant was 8% of the total dry weight (FIG. 6). As described in Example 10, when seeds obtained by self-pollination were germinated in the presence of kanamycin and examined for segregation of the antibiotic-resistant phenotype, a ratio of 1 (sensitive) to 4 (resistant) was observed. This suggests that integration of the selectable marker and TP-CPL had occurred at a single location in the genome, as opposed to a double-loci event that that would have resulted a kanamycin-resistance segregation ratio of 1:15. Theoretically, the kanamycin-resistant plants consist of two populations, heterozygotes and homozygotes, present in a ratio of 2:1. Assuming the absence of co-suppression, the homozygous plants would be expected to have twice as much CPL enzyme activity as the heterozygous plants, and perhaps accumulate even higher levels of pHBA glucosides. To address this issue, 5 of the kanamycin-resistant seedlings (referred to below as #34 A–34 E) were grown to mature plants and analyzed for CPL enzyme activity and pHBA glucosides. The plants were 15-weeks-old at the time the samples were taken, and the results of this study are shown in Table I below.

TABLE I

| Plant 34 Sibling | CPL Enzyme Activity (pkat/mg protein) | Total pHBA-glucosides (percent of dry weight) |
| --- | --- | --- |
| 34A | 927 | 4.8 |
| 34B | 991 | 5.9 |
| 34C | 1048 | 5.0 |
| 34D | 784 | 5.0 |
| 34E | 356 | 3.2 |

As anticipated, all of the seedlings that were kanamycin-resistant also exhibited CPL enzyme activity and accumulated pHBA glucosides. Thus, the gene for the artificial fusion protein, TP-CPL, was stably passed on to the next generation. Although the number of plants that was examined is small, there appeared to be two different populations. The CPL enzyme activities for four of the offspring (e.g., #34A–34D) were very similar, ranging from 784–1,048 pkats per mg of protein. Note that the average CPL activity for this group (e.g., 938 pkat/mg) is about 4.5-times higher than the best value that was obtained with TP-UbiC when living tobacco plants were examined (Siebert et al., Plant Physiol. 112:811–819 (1996)). The same four siblings also had comparable levels of pHBA glucosides. The average value was ~5.2% of dry weight, and the numbers were closely clustered (e.g., 4.8%–5.9%).

In contrast, one of the plants (e.g., #34E) had much lower levels of CPL enzyme activity and pHBA glucosides. While it is tempting to speculate that this sibling is a heterozygote and the other four plants are homozygotes, it is still too premature to draw this conclusion. First, based on the segregation pattern that was obtained for the kanamycin-resistant phenotype, only one third of the plants would be expected to be homozygous, not the observed 80% of the population. Second, it is conceivable that the homozygous state with twice as many copies of the trait gene could lead to co-suppression, resulting in paradoxically low levels of CPL enzyme activity and pHBA glucosides. Experiments are currently under way to try to resolve this issue. Regardless, it is interesting to note that the accumulation of pHBA glucosides in the second generation plants was not quite as high as it was in the primary transformant.

Example 13

Proteolytic Processing of TP-CPL Occurs at the Predicted Cleavage Site In Vivo

As shown in FIG. 7, whole leaf extracts of transgenic tobacco plants expressing the artificial fusion protein, TP-CPL, contain only a single polypeptide that cross-reacts with antisera directed against purified recombinant E. coli CPL. Moreover, the size of the cross-reacting polypeptide, which is not present in wildtype plants, is much smaller than the original fusion protein that was introduced into tobacco, as determined by SDS-PAGE. In fact, it appears to co-migrate precisely with purified recombinant ΔTP-CPL, the predicted chloroplast cleavage product of TP-CPL (Example 4) and the radioactive band that is observed after in vitro chloroplast import experiments (Example 5). Nevertheless, to provide an unequivocal demonstration that the removal of the chloroplast targeting sequence from the artificial fusion protein does occur at the predicted cleavage site in vivo, the protein was purified from leaf tissue obtained from tobacco Transformant #34 and its N-terminal amino acid residues were determined by Edman degradation.

Leaf tissue (6.9 g wet weight) was homogenized in a mortar and pestle with an ice-cold solution containing 50 mM Tris-HCl (pH 7.5), 1 mM EDTA, 0.1% β-mercaptoethanol, 1 mM phenylmethanesulfonyl fluoride, and 75 mg/ml polyvinylpolypyrrolidone (grind buffer). Unless otherwise specified, all subsequent steps were conducted at 0–4° C. The leaf extract was centrifuged for 30 min (40,000× g) to remove insoluble material, and the resulting supernatant was supplemented with solid $(NH_4)_2SO_4$ to final concentration of 80% (w/v). The solution was gently stirred for 30 min, and was then centrifuged for 10 min at 20,000× g to precipitate the majority of proteins. The supernatant was discarded, and the resulting pellet was resuspendend in 2.0 ml of grind buffer without polyvinylpolypyrrolidone that was supplemented with 8% (v/v) glycerol, at a protein concentration of 14.3 mg per ml, as determined by the Bio-Rad (Bradford) protein assay.

An aliquot of the above sample (0.5 ml) was then exchanged into Buffer Q (Example 2), using a PD-10 gel filtration column (Pharmacia Biotech Inc). After the sample had completely entered the resin, the column was washed once with 2.2 ml of Buffer Q and the eluent was discarded. The material eluting in the void volume was then collected, after the addition of another 1.1 ml of the same buffer. The entire sample was then applied to a MonoQ HR5/5 column that was equilibrated at room temperature with Buffer Q. The column was developed with the same buffer at a flow rate of 1.0 ml/min, and fractions (1.0 ml each) were collected from the time of sample injection. Fractions containing the chloroplast cleavage product of TP-CPL were identified by Western blot analysis, using antisera directed against purified recombinant E. coli CPL. Virtually all of the cross-reacting material eluted in fractions #3 and #4, and as before the only species that was detected with the antisera co-migrated with purified, recombinant ΔTP-CPL. Column fractions #3 and #4 were pooled, supplemented with 7.5% glycerol, 0.3 M NaCl and 0.01% Tween 20 (Bio-Rad cat. # 170-6531), and concentrated to a final volume of about 200 µl using a Centricon 10 (Amicon). The entire sample was then applied to a 7.5×600 mm TSK G3000SW gel filtration column (TOSOH Corp.) that was pre-equilibrated at room temperature with 50 mM Tris-HCL (pH 7.2), 0.3 M NaCl, and 0.01% Tween 20. The column was developed at 1.0 ml/min (25° C.) with the same buffer, and fractions eluting between 21.5–23 min, which contained the authentic TP-CPL chloroplast cleavage product, were pooled together and concentrated to a final volume of 55 µl using Microcon 10 (Amicon). The concentrated material was diluted 1:1 with sample buffer, and analyzed by SDS-PAGE to assess the degree of purification. Although a number of other bands were also evident in the Coomassie blue-stained gel, the TP-CPL chloroplast cleavage product was a major protein species, well separated from other contaminants. N-terminal analysis of the polypeptide corresponding to this band (following electophoretic transfer to a polyvinylidene difluoride membrane and 6 cycles of Edman degradation) confirmed that proteolytic processing of the artificial fusion protein had occurred at the predicted cleavage site; e.g., at the Cys-Met junction indicated in FIG. 1. From this observation and the enzyme activity data presented in Example 4, it may be concluded that the polypeptide that is responsible for the conversion of chorismate to pHBA in chloroplasts of tobacco plants expressing TP-CPL, is a fully-active CPL variant with 5 additional amino acid residues attached to its N-terminus.

Example 14

Generation and Analysis of Transgenic Arabidopsis Plants Expressing TP-CPL

The artificial fusion protein, TP-CPL, was introduced into arabidopsis and pHBA glucoside levels were determined. The binary vector carrying the CaMV35S-CPL expression cassette (e.g., TP-CPL-pZBL1) was transformed into *Agrobacterium tumefaciens* strain C58 C1 Rif (also known as strain GV3101), carrying the disarmed Ti (virulence) plasmid pMP90 (Koncz, C. and Schell, J. (1986) *Mol. Gen. Genet.* 204:383–396) by electroporation, using available protocols (Meyer et al. (1994) *Science* 264:1452–1455). The MP90 strain carrying the binary vector with the CPL expression construct was used to transform *Arabidopsis thaliana* plants of the ecotype Columbia with wild type, fah1-2 (Chapple et al., *Plant Cell* 4:1413–1424 (1992)), sng1-1 (Lorenzen et al., *Plant Physiology* 112:1625–1630 (1996)) genetic backgrounds using a published protocol of the vacuum infiltration technique (Clough S. J., Bent A. F. (1998) *Plant J.* 16(6):735–43). Transgenic seedlings were identified under sterile conditions on standard plant growth media using kanamycin (50 µg/ml) for selection. Kanamycin resistant seedlings were transferred to soil and cultivated under a 12-hour light/12-hour dark photoperiod at 100 E $m^{-2}s^{-1}$ at 18° C. (dark) and 21° C. (light) in a soil/perlite mixture. Through this procedure, a population of 301 primary transformants derived from independent transformation events was generated. Six weeks after transfer to soil, the transgenic arabidopsis plants were analyzed for pHBA glucosides using reverse phase HPLC as described below.

Fresh cut leaf material was homogenized in 50% MeOH (5 µl per mg wet weight), and the resulting extracts were clarified by low-speed centrifugation. An aliquot of the leaf extract was then applied to a Nova-Pak C18 column (60 angstrom pore size, 4 µm particle size) using a gradient of acetonitrile (6%–48%) that contained 1.5% phosphoric acid. The pHBA phenolic and ester glucosides were detected by UV absorption at 254 nm, and quantitated using extinction coefficients that were obtained from authentic chemical standards (cf. Example 8). Of the 272 transgenic arabidopsis plants that were analyzed, 239 (or ~88%) contained detectable levels of both glucose conjugates, and these were present in about equal amounts. The total pHBA glucoside content of the best overproducer was 10.73% of dry weight, which is very similar to the highest levels that were observed with tobacco using the same construct. The mean value for the entire population of transgenic arabidopsis plants was 3.35% (+/−0.13%); the number in parenthesis is the standard error of the mean.

Taken together, these results clearly demonstrates that the instant chimeric protein, TP-CPL, is able to generate high levels of pHBA glucosides not only in tobacco, but in other plant species as well.

What is claimed is:

1. A method for the production of unconjugated para-hydroxy benzoic acid comprising:
  a) providing a plant having an endogenous source of chorismate and containing a chorismate pyruvate lyase expression cassette comprising a nucleic acid sequence encoding a chimeric protein comprising SEQ ID NO:8;
  b) growing said plant under conditions whereby the chimeric protein is expressed and translocated to the chloroplast for the conversion of chorismate to para-hydroxy benzoic acid and subsequent conversion to para-hydroxy benzoic acid glucoside by endogenous plant enzymes;
  c) recovering para-hydroxy benzoic acid and para-hydroxy benzoic acid glucoside from the plant; and
  d) hydrolyzing the para-hydroxy benzoic acid glucoside and recovering unconjugated para-hydroxy benzoic acid.

2. A method according to claim 1 wherein the nucleic acid encoding the chimeric protein is operably linked to a promoter selected from the group consisting of the 35S promoter, the nopaline synthase promoter, the octopine synthase promoter, cauliflower mosaic virus promoter, the ribulose-1,5-bisphosphate carboxylase promoter and the promoter of the chlorophyll a/b binding protein.

3. A method according to claim 1 wherein the chimeric protein expressed in said plant is proteolytically cleaved in chloroplasts to yield a chorismate pyruvate lyase variant having the amino acid sequence as set forth in SEQ ID NO:16.

4. A method according to claim 1 wherein the para-hydroxy benzoic acid glucoside is produced at a concentration of a least 2% para-hydroxy benzoic acid glucoside per dry weight of plant leaf biomass.

5. A method according to claim 1 wherein the para-hydroxy benzoic acid glucoside is produced at a concentration of at least 10% para-hydroxy benzoic acid glucoside per dry weight of plant leaf biomass.

6. A method according to claim 1 wherein the plant containing a chorismate pyruvate lyase expression cassette is selected from the group consisting of soybean, tobacco, Arabidopsis, sugar beet, and sugar cane.

7. A method according to claim 1 wherein the para-hydroxy benzoic acid is produced at a concentration of greater than 4.5% para-hydroxy benzoic acid per dry weight of plant biomass.

* * * * *